(12) United States Patent
Bazan et al.

(10) Patent No.: US 7,811,755 B2
(45) Date of Patent: Oct. 12, 2010

(54) METHODS AND ARTICLES FOR STRAND-SPECIFIC POLYNUCLEOTIDE DETECTION WITH CATIONIC MULTICHROMOPHORES

(75) Inventors: Guillermo C. Bazan, Santa Barbara, CA (US); Bin Liu, Singapore (SG)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/329,861

(22) Filed: Jan. 10, 2006

(65) Prior Publication Data

US 2006/0216734 A1   Sep. 28, 2006

Related U.S. Application Data

(60) Provisional application No. 60/642,883, filed on Jan. 10, 2005.

(51) Int. Cl.
*C12Q 1/68* (2006.01)
*C12M 1/34* (2006.01)
*C12M 3/00* (2006.01)

(52) U.S. Cl. .............. 435/6; 435/287.2; 536/22.1; 536/23.1; 536/24.3; 536/26.6

(58) Field of Classification Search .............. 435/6, 435/287.2; 536/22.1, 23.1, 24.3, 26.6
See application file for complete search history.

(56) References Cited

U.S. PATENT DOCUMENTS

| | | |
|---|---|---|
| 4,948,843 A | 8/1990 | Roberts et al. |
| 4,950,587 A | 8/1990 | Roberts et al. |
| 5,408,109 A | 4/1995 | Heeger et al. |
| 5,612,221 A | 3/1997 | Simons et al. |
| 5,869,350 A | 2/1999 | Heeger et al. |
| 5,881,083 A | 3/1999 | Diaz-Garcia et al. |
| 5,968,762 A | 10/1999 | Jadamec et al. |
| 5,990,479 A | 11/1999 | Weis et al. |
| 6,090,552 A | 7/2000 | Nazarenko et al. |
| 6,263,286 B1 | 7/2001 | Gilmanshin et al. |
| 6,280,933 B1 | 8/2001 | Glazer et al. |
| 6,350,431 B1 | 2/2002 | Snow et al. |
| 6,534,329 B2 | 3/2003 | Heeger et al. |

(Continued)

FOREIGN PATENT DOCUMENTS

EP        1279023        1/2003

(Continued)

OTHER PUBLICATIONS

Gaylord et al, DNA detection using water soluble conjugated polymers and peptide nucleic acid probes, 2002, PNAS, 99, 10954-10957.*

(Continued)

*Primary Examiner*—Stephen Kapushoc
*Assistant Examiner*—Narayan K Bhat
(74) *Attorney, Agent, or Firm*—David W. Maher; TechLaw LLP

(57) ABSTRACT

The invention relates to methods, articles and compositions for the detection and analysis of biomolecules in a sample. Provided assays include those determining the presence of a target biomolecule in a sample or its relative amount, or the assays may be quantitative or semi-quantitative. The methods can be performed in an array format on a substrate.

37 Claims, 12 Drawing Sheets

U.S. PATENT DOCUMENTS

| | | | |
|---|---|---|---|
| 6,545,164 | B1 | 4/2003 | Waggoner et al. |
| 6,579,726 | B1 * | 6/2003 | Natan et al. .................. 436/518 |
| 6,589,731 | B1 | 7/2003 | Chen et al. |
| 6,743,640 | B2 | 6/2004 | Whitten |
| 6,951,682 | B1 | 10/2005 | Zebala |
| 6,979,543 | B2 | 12/2005 | Chen et al. |
| 7,122,383 | B2 | 10/2006 | Jones et al. |
| 7,141,437 | B2 | 11/2006 | Dvornic et al. |
| 7,208,122 | B2 | 4/2007 | Swager et al. |
| 2001/0026921 | A1 | 10/2001 | Rabbani et al. |
| 2002/0009728 | A1 | 1/2002 | Bittner |
| 2002/0034747 | A1 | 3/2002 | Bruchez |
| 2002/0150759 | A1 | 10/2002 | Jones |
| 2002/0177136 | A1 | 11/2002 | McBranch et al. |
| 2003/0054413 | A1 | 3/2003 | Kumaraswamy |
| 2003/0087311 | A1 | 5/2003 | Wolf |
| 2004/0009506 | A1 | 1/2004 | Stephan et al. |
| 2004/0023248 | A1 * | 2/2004 | O'Malley ....................... 435/6 |
| 2004/0023317 | A1 | 2/2004 | Motamedi et al. |
| 2004/0142344 | A1 | 7/2004 | Bazan |
| 2004/0219556 | A1 | 11/2004 | Bazan |
| 2004/0241768 | A1 | 12/2004 | Whitten et al. |
| 2005/0003386 | A1 | 1/2005 | Bazan |
| 2005/0059168 | A1 | 3/2005 | Bazan |
| 2005/0064239 | A1 * | 3/2005 | Takei ......................... 428/690 |
| 2005/0064604 | A1 | 3/2005 | Bohmann et al. |
| 2005/0196775 | A1 | 9/2005 | Swager et al. |
| 2006/0073607 | A1 | 4/2006 | Rose et al. |
| 2006/0127929 | A1 | 6/2006 | Swager |
| 2006/0175193 | A1 | 8/2006 | Inganas et al. |
| 2006/0183140 | A1 | 8/2006 | Bazan |
| 2006/0204984 | A1 | 9/2006 | Bazan |
| 2006/0216734 | A1 | 9/2006 | Bazan |
| 2006/0216759 | A1 | 9/2006 | Nassani |
| 2007/0178470 | A1 | 8/2007 | Bissonnette et al. |
| 2008/0038751 | A1 | 2/2008 | Asberg et al. |

FOREIGN PATENT DOCUMENTS

| | | |
|---|---|---|
| EP | 1281744 | 2/2003 |
| EP | 0990903 B1 | 3/2003 |
| EP | 0684239 B1 | 12/2003 |
| EP | 0708837 | 3/2006 |
| WO | WO 99/35288 | 7/1999 |
| WO | WO 99/35288 A1 | 7/1999 |
| WO | WO 00/14278 | 3/2000 |
| WO | WO 00/14278 A1 | 3/2000 |
| WO | WO 00/66790 | 11/2000 |
| WO | WO 00/66790 A1 | 11/2000 |
| WO | WO 01/01144 * | 1/2001 |
| WO | WO 01/95059 * | 12/2001 |
| WO | WO 02/081735 | 10/2002 |
| WO | WO 02/081735 A2 | 10/2002 |
| WO | WO 02/084271 | 10/2002 |
| WO | WO 04/001379 | 12/2003 |
| WO | WO 04/001379 A2 | 12/2003 |
| WO | WO 2004/037886 | 5/2004 |
| WO | WO 2004/077014 | 9/2004 |
| WO | WO 2005/056628 | 6/2005 |
| WO | WO 2006/092063 | 9/2006 |
| WO | WO 2007/001438 | 1/2007 |

OTHER PUBLICATIONS

Balakin, K.V. et al. Conjugates of oligonucleotides with polyaromatic fluorophores as promising DNA probes[1;] *Biosensors and Bioelectronics* (1998) 13:771-778.

Bardea, A. et al. Sensing and amplification of oligonucleotide-DNA interactions by means of Impedance spectroscopy: a route to a Tay-Sachs sensor, *Chem. Commun.* (1999) 21-22.

Baur, J.W., et al. Thin-Film Light-Emitting Devices Based on Sequentially Adsorbed Multilayers of Water-Soluble Poly (p-phenylene)s; *Advanced Materials* (1998) 10:17:1452-1455.

Behr, J.P. Synthetic Gene-Transfer Vectors; *Acc. Chem. Res.* (1993) 26: 274-278.

Behr, J.P. DNA Strongly Binds to Micelles and Vesicles Containing Lipopolyamines or Lipointeircalants; *Tetrahedron Lett.* (1986) 27:48:5861-5864.

Benson, S.C. et al. Heterodimeric DNA-binding dyes designed for energy transfer: synthesis and spectroscopic properties; *Nucleic Acids Res.* (1993) 21:24:5727-5735.

Betts, L., et al, A Nucleic Acid Triple Helix Formed by a Peptide Nucleic Acid-DNA Complex; *Science* (1995) 270: 1838-1841.

Bhattacharya, S. and Mandal, S.S. Interaction of surfactants with DNA. Role of hydrophobic y and surface charge on intercalation and DNA melting; *Blochim.et Blophys. Acta*; (1997) 1323:29-44.

Bhattacharya, S. and Mandal, S.S. Role of hydrophobic effect and surface charge in surfactan DNA association; *Indian J. Biochem. & Biophys.* (1997) 34:11-17.

Bier, F.F. And Kleinjung, F. Feature-size limitations of microarray technology—a critical reviews *Fresenius J. Anal. Chem.* (2001) 371:151-156.

Birnboim, H.C. and Jevcak, J.J. Fluorometric Method for Rapid Detection of DNA Strand Breaks in Human White Blood Cells Produced by Low Doses of Radiation; *Cancer Res.* (1981) 41:1889-1892.

Blessing, T. et al. Monomolecular collapse of plasmid DNA into stable virus-like particles; *Proc. Na'l . Acad. Sci. USA* (1998) 95:1427-1431.

Bronich, T.K. et al. Recognition of DNA Topology in Reactions between Plasmid DNA and Cationic Copolymers; *J. Am. Chem. Soc.* (2000) 122:35:8339-8343.

Cardullo, R.A. et al. Detection of nucleic acid hybridization by nonradiative fluorescence resonance energy transfer, *Proc. Natl. Acad. Sci. USA* (1988) 85:8790-8794.

Castro, A. and Williams, J.G.K. Single-molecule detection of specific nucleic acid sequences in unamplified genomic DNA; *Anal. Chem.* (1997) 69:19:3915-3920.

Chandar, P. et al. Fluorescence probe Investigation of anionic polymer-cationic surfactant interactions; *Macromolecules* (1988) 21:950-953.

Chehab, F.F. and Kan, Y.W. Detection of specific DNA sequences by fluorescence amplification: A color complementation assay; *Proc. Natl. Acad. Sci. USA* (1989) 86:9178-9182.

Chen, L and Frankel, A.D. A peptide Interaction in the major groove of RNA resembles protein Interactions in the minor groove of DNA; *Proc. Natl. Acad. Sci. USA.* (1995) 92:5077-5081.

Chen, L. et al. Highly sensitive biological and chemical sensors based on reversible fluorescence quenching in a conjugated polymer; *Proc. Natl. Acad. Sci. USA.* (1999) 96:22:12287-12292.

Chen, W. et al. Using Ethidium Bromide to Probe the Interactions between DSA and Dendrimers; *Langmuir* (2000) 16:15-19.

Delling, U. et al. The number of positively charged amino acids in the basic domain of Tat Is critical for trans-activation and complex formation with TAR RNA; *Proc. Natl. Acad. Sci . USA* (1991) 88:6234-6238.

Demidov, V.V. PNA and LNA throw light on DNA; *Trends in Biotechnology* (2003) 21:1:4-7.

Demidov, V.V. et al. Stability of peptide nucleic acids in human serum and cellular extracts; *Biochem. Pharmacol.* (1994)48:6:1310-1313.

Didenko, V.V. DNA Probes Using Fluorescence Resonance Energy Transfer (FRET): Designs and Applications; *BioTechniques* (2001) 31:5:1106-1121.

Dogariu, A. et al. Time-resolved Förster energy transfer in polymer blends; *Synthetic Metals* (1999): 100:95-100.

Dufourco, J. et al. Molecular assembling of DNA with amphipathic peptides; *FEBS Lett.* (1998) 421;7-11.

Eastman, S.J. et al. Biophysical characterization of cationic lipid: DNA complexes; *Blochim. et Biolphys. Acta* (1997) 1325:41-62.

Egholm, M. et al. PNA hybridizes to complementary oligonucleotides obeying the Watson-Crick hydrogenbonding rules; *Nature* (1993) 365:566-568.

Egholm, M. et al. Recognition of Guanine and Adenine in DNA by Cytosine and Thymine Containing Peptide Nucleic Acids (PNA); *J. Am. Chem. Soc.* (1992) 114:9677-9678.

Englebienne, P. Synthetic materials capable of reporting biomolecular recognition events by chronic transition; *J. Mater Chem.* (1999) 9:1043-1054.

Eskilsson, K. et al. DNA-Surfactant Complexes at Solid Surfaces; *Langmuir* (2001)17:1666-1689.

Felgner, P.L. et al. Nomendature for Synthetic Gene Delivery Systems; *Hum. Gene Ther.* (1997) 8:511-512.

Ferguson, B.Q. and Yang, D.C.H. Localization of Noncovalently Bound Ethidium in Free and Methlonyl-tRNA Synthetase Bound tRNA$^{tMET}$ by Singlet-Singlet Energy Transfer; *Biochemistry* (1986) 25:5298-5304.

Fernandez-Saiz, M. et al. A Cationic Cydophane That Forms a Base-Pair Open CoMplex with RNA Duplexes; *J. Am. Chem. Soc.* (1996)118:4739-4745.

Frankel, A.D. Peptide models of the Tat-TAR protein-RNA interaction; *Prot. Sci.* (1992)1:1539-1542.

Futami, J. et al. Optimum Modification for the Highest Cytotoxicity of Catlonized Ribonuclease; *J. Biochem.* (2002) 132:223-228.

Gallego, J. and Varani, G. Targeting RNA with Small-Molecule Drugs: Therapeutic Promise and Chemical Challenges; *Acc. Chem. Res.* (2001) 34:10:836-843.

Gallo, R and Montagnier, L AIDS in 1988; *Sci. Am.* (1988) 259:4: 41-48.

Ganachaud, F. et al. Adsorption of Single-Stranded DNA Fragments onto Cationic Aminated Latex Particles; *Langmuir* (1997) 13:701-707.

Gaylord, B. S. et al. DNA detection using water-soluble conjugated polymers and peptide nucleic acid probes; *Proc. Natl. Acad. Sci. USA* (2002) 99:17:10954-10957.

Gaylord, B.S. et al. Water-Soluble Conjugated Oligomers: Effect of Chain Length and Aggregation on Photoluminescence-Quenching Efficiencies; *J. Am. Chem. Soc.* (2001) 123:6417-6418.

Gaylord, B.S. et al. DNA Hybridization Detection with Water-Soluble Conjugated Polymers and Chromophore-Labeled Single-Stranded DNA; *J. Am. Chem. Soc.* (2003) 125:896-900.

Gershon, H, et al. Mode of Formation and Structural Features of DNA-Cationic Liposome Complexes Used for Transfection; *Biochemistry* (1993) 32:7143-7151.

Giesen, U. et al. A formula for thermal stability ($^{T}$m) prediction of PNA/DNA duplexes; *Nucleic Acids Res.* (1998) 26:21:5004-5006.

Gössl, L at al. Molecular Structure of Single DNA Complexes with Positively Charged Dendronized Polymers; *J. Am. Chem. Soc.* (2002) 124:6860-6865.

Hage, D.S.. Immunoassays; *Anal. Chem.* (1999) 71:12:294R-304R.

Hanvey, J.C. et al. Antisense and Antigens Properties of Peptide Nucleic Acids: *Science* (1992) 258:1481-1485.

Harada, A. and Kataoka, K. Chain Length Recognition: Core-Shell Supramolecular Assembly from Oppositely Charged Block Copolymers; *Science* (1999) 283:65-67.

Ho, H.A. et al. Colorimetric and Fluorometric Detection of Nucleic Acids Using Cationic Polythiophene Deriatives; *Angew. Chem. Int. Ed.* (2002) 41:9:1548-1551.

Izumrudov, V.A. et al. The Influence of chain length of a competitive polyanlon and nature of monovalent counterions on the direction of the substitution reaction of polyelectrolyte complexes; *Makromol. Chem. Rapid Commun.* (1988) 9:7-12.

Izumrudov, V.A. et al. Competitive Reactions in Solutions of DNA and Water-Soluble Interpolyelectrolyte Complexes; *Biopolymers* (1995) 35:523-531.

Izumrudov, V.A. et al. Competitive Displacement of Ethidium Cations Intercalated in DNA by Polycattions; *Dokl. Phys. Chem.* (1995) 342:Nos. 4-6: 150-153.

Izumrudov, V.A. et al. Ethidium Bromide as a Promising Probe for Studying DNA Interaction with Cationic Amphiphiles and Stability of the Resulting Complexes; *Langmuir* (2002) 18:10348-10356.

Izumrudov, V.A. et al. Controllable Stability of DNA-Containing Polyelectrolyte Complexes in Water-Salt Solutions; *Biopolymers.* (1999) 52:94-108.

Izumrudov, V.A. and Zhiryakova, M.V. Stability of DNA-containing Interpolyelectrolyte complexes in water-salt solutions; *Macromol. Chem. Phys.* (1999) 200:11:2533-2540.

Jain, C. and Belasco, J.G. Rapid Genetic Analysis of RNA-Protein Interactions by Translational Repression in *Escherichia coli; Methods Enzymol.* (2000) 318:309-332.

Jenkins, Y. and Barton, J.K. A Sequence-Specific Molecular Light Switch: Tethering of an Oligonucleotide to a Dlpyridophenazine Complex of Ruthenium (II); *J. Am. Chem. Soc.* (1992) 114:8736-8738.

Johansson, M.K. et al. Intramolecular Dimers: A New Strategy to Fluorescence Quenching in Dual-Labeled Oligonucleotide Probes; *J. Am. Chem. Soc.* (2002) 124:6950-6958.

Kabanov, V.A. et al. DNA Interpilyeletrolyte Complexes as a Tool for Efficient D Cell Transformantin; *Biopolymers.* (1961) 31;1437-1443.

Kabanov, A.V. and Kabanov, V.A. DNA Complexes with Polycations for the Delivery of Genetic Material Into Cells; *Bioconjugate Chem.* (1995) 6:7-20.

Kabanov, V.A. et al. Cooperative Interpolyelectrolyte Reactions; *Makromol. Chem. Suppl.* (1985)13;137-155.

Karn, J. et al. HIV A Practical Approach; RNA binding assays for the regulatory proteins Tat and Rev; *IRL Press, New York;* (1995) 9:147-165.

Katayose, S. and Kataoka, K. Water-Soluble Polyion Complex Associates of DNA and Poly(ethylene glycol)-Poly(L-lysine) Block Copolymer; *Bioconjugate Chem.* (1997) 8:702-707.

Kircheis, R. et al. Tumor targeting with surface-shielded ligand-polycation DNA complexes; *J. Controlled Release*; (2001) 72:165-170.

Kirsh, Yu. E. et al. Comparision of Properties of an Oxime-Bound Partially Quaternized Poly-4-Vinylpyridine and a Monomer Analogous Oxime; *Eur. Polym. J.* (1974) 10:393-399.

Knemeyer, J. et al. *Probes for Detection of Specific DNA . . . Anal. Chem*(2000) 72:3717-3724.

Kwon, I.C. et al. Electrically Erodible polymer gel for controlled release of drugs; *Nature* (1991) 354:291-293.

Leclerc M. Optical and Electrochemical Transducers Based on Functionalized Conjugated Polymers; *Adv. Mater*, (1999) 11:18:1491-1498.

Lee, M.A. et al. ResonSense®: simple linear fluorescent probes for quantitative homogeneous rapid polymerase chain reaction; *Anal. Chlm. Acta* (2002).457:61-70.

Le-Pecq, J.B. and Paoletti, C. A Fluorescent Complex between Ethidium Bromide and Nucleic Acids; *J. Mol Biol.* (1967) 27:87-106.

Leulliot, N. and Varani, G. Current Topics in RNA-Protein Recognition: Control of Specificity and Biological Function through Induced Fit and Conformational Capture; *Biochemistry* (2001) 40:27:7947-7956.

Liu, B. et al. Effect of Chromophore-Charge Distance on the Energy Transfer Properties of Water-Soluble Conjugated Oligomers; *J. Am. Chem. Soc.* (2003) 125:6705-6714.

Makino, S. et al. Molecular Characterizatlon and Protein Analysis of the *cap* Region, Which Is Essential for Encapsulatlon in *Bacillus anthracis; J. Bacteriol.* (1989) 171:2:722-730.

Manning, G.S. Thermodynamic Stability Theory for DNA Doughnut Shapes Induced by Charge Neutrallzation; *Blopolymers.* (1980) 19:37-59.

Manning, G.S. The Possibillity of Intrinsic Local Curvature in DNA Toroids; *Blopolymers.* (1981) 20:1261-1270.

Manning, G.S. The molecular theory of polyelectrolyte solutions with applications to the electrostatic properties of polynucleotides; *Qrtly Review of Biophysics.* (1978) v.11: 179-246.

Maruyama, A. et al. Characterization of Interpolyelectrolyte Complexes between Double-Stranded DNA and Polylsine Comb-Type Copolymers Having Hydrophilic Side Chains; *Bloconjugate Chem.* 1998 9:292-299.

Matsumoto, C; et al. High-Throughput Screening Utilizing intramolecular Fluorescence Resonance Energy Transfer for the Discovery of the Moleculesihat Bind HIV-1 TAR RNA Specifically; *Bioorg. Med. Chem. Lett.* (2000) 10:1857-1861.

McLoughun, D.M. et al. A simple and effective separation and purification procedure for DNA fragments using Dodecyltrimethylammonium bromide; *Bioseparation.* (2001) 9:307-313.

McQuade, D.T. et al. Conjugated Polymer-Based Chemical Sensors; *Chem. Rev.* (2000)100:2537-2574.

McQuade, D.T. et al. Signal amplification of a "Turn-On" Sensor: Harvesting the Light Captured by a Conjugated Polymer; *J. Am. Chem. Soc.* (2000)122:12389-12390.

Mel'Nikov, S.M. et al. Discrete Coil—Globule Transition of Large DNA induced by Cationic Surfactant; *J. Am. Chem. Soc.* (1995) 117:2401-2408.

Mergny, J.L. et al. Fluorescence Energy Transfer between Two Triple Helix-Forming Oligonudeotides Bound to Duplex DNA; *Biochemistry.* (1994) 33:15321-15328.

Miao, Y.J. et al. Photophysics of Poly(paracydophan-1-ene) and Derivatives: Evidence for intrachain Energy Transfer and Chromophore Aggregation; *J. Am. Chem. Soc.* (1995) 117:11407-11420.

Miller, I.R. and Bach, D. Interaction of DNA with Heavy Metal Ions and Polybases: Cooperative Phenomena; *Biopolymers.* (1968) 6:169-179.

Minehan, D.S. et al. Kinetics of DNA Binding to Electrically Conducting Polypyrrole Films; *Macromolecules.* (1994) 27:777-783.

Morgan, A.R. and Pulleyblank, D.E. Native and Denatured DNA, Cross-Linked and Palindromic DNA and Circular Covalently-Closed DNA Analysed by a Sensitive Fluorometric Procedure; *Biochem. Blophys. Res. Commun.* (1974) 61:2:396-403.

Nielsen, P.E. Applications of peptide nudeic acids, *Analytical biotechnology.* (1999) 10:71-75.

Nguyen, H-K, et al. Nonviral Transfer Technology: Evaluation of polyether-polyethyleneimine graft copolymers as gene transfer agents; *Gene Ther.* (2000) 7:126-138.

Nishanian, P. et al. A Simple Method for improved Assay Demonstrates that HIV p24 Antigen Is Present as Immune Complexes in Most Sera from HIV-Infected Individuals; *J. Infect. Dis.* (1990) 162:21-28.

Nuovo, G.J. In Situ Localization of PCR-Amplified DNA and cDNA: *Methods Mol. Bio.* (2000) 123:217-238.

Olins, D.E. et al. Model Nucleoprotein Complexes: Studies on the Interaction of Cationic Homopolypeptides with DNA; *J. Mol. Biol.* (1967) 24:157-176.

Pasternack, R.F: et al. Long-Range Fluorescence Quenching of Ethldium Ion by Cationic Porphyrins in the Presence of DNA; *J. Am. Chem. Soc.* (1991) 113:6835-6840.

Patolsky, F. et al. Amplified DNA Detection by Electrogenerated Biochemlluminescence and by the Catalyzed Precipitation of an Insoluble Product on Electrodes in the Presence of the Doxorubicin intercalator; *Angew. Chem. Int. Ed.* (2002) 41:18:3398-3402.

Patolsky, F. et al. Electronic Transduction of DNA Sensing Processes on Surfaces: Amplification of DNA Detection and Analysis of Single-Base Mismatches by Tagged Liposomes; *J. Am Chem. Soc.* (2001):123:5194-5205.

Peterlinz, K.P. et al. Observation of Hybridization and Dehybridizatlon of Thiol-Tethered DNA using Two-Color Surface Plasmon Resonance Spectroscopy; *J. Am. Chem. Soc.* (1997) 119:3401-3402.

Petty; J.T. et al. Thermodynamic Characterization of the Association of Cyanine Dyes with DNA; *J. Phys. Chem. B.* (2000) 104:7221-7227.

Pilipenko, E.V. et al. A cell cycle-dependent protein serves as a template-specific translation Initiation factor; *Genes & Dev.* (2000) 14:2028-2045.

Pinto, M.R. and Schanze, K.S. Conjugated Polyelectrolytes: Synthesis and Applications; *Synthesis.* (2002). 9:1293-1309.

Plank, C. et al. Branched Cationic Peptides for Gene Delivery: Role of Type and Number of Cationic Residues in Formation and *in Vitro* Activity of DNA Polyplexes; *Hum. Gene Ther.* (1999) 10:319-332.

Portela, A. and Digard, P. The Influenza virus nucleoprotein: a multifunctional RNA-binding protein pivotal to virus replication; *J. Gen. Virol.* (2002) 83:723-734.

Puglisi, J.D. et al. Conformation of the TAR RNA-Arginine Complex by NMR Spectroscopy; *Science.* (1992) 257:76-80.

Pullman, B. et al. Two Aspects of DNA Polymorphism and Microheterogeneity: Molecular Electrostatic Potential and Steric Accesiblilty; *J. Blochem.* (1982) 124:229-238.

Richter, S. et al. Specific HIV-1 TAR RNA Loop Sequence and Functional Groups pre Required for Human Cyclin T1-Tat-TAR Ternary Complex Formation; *Biochemistry.* (2002) 41:8391-8397.

Saghatelian, A. et al. DNA Detection and Signal Amplification via an Engineered Allosteric Enzyme; *J. Am. Chem. Soc.* (2003) 125:344-345.

Saiki, R.K. et al. Enzymatic Amplification of $\beta$-Globin Genomic Sequences and Restriction Site Analysis for Diagnosis of Sickle Cell Enemla; *Science.* (1985) 230:1350-1354.

Schork, N.J. et al. Single nucleotide polymorphisms and the future of genetic epidemiology; *Clin. Genet.* (2000) 58:250-264.

Seymour, L.W. et al. Cationic block copolymers as self-assembling vectors for gene delivery; *Self-assembling Complexes for Gene Delivery;* (1998) 11:219-239.

Shinozuka, K. et al. A Novel Multifunctionality Labelled DNA Probe Bearing an Intercalator and a Fluorophore; *J. Chem. Chem. Soc., Chem. Commun.* (1994) 1377-1378.

De Smedt, S.C: et al. Cationic Polymer Based Gene Delivery Systems; *Pharm. Res.* (2000) 17:2:113-126.

Smith, J.O. et al. Molecular Recognition of PNA-Containing Hybrids: Spontaneous Assembly of Helical Cyanine Dye Aggregates on PNA Templates; *J. Am. Chem. Soc.* (1999) 121:2686-2695.

Smith, P. et al. Surfactant structure around DNA in aqueous solution; *Phys. Chem. Chem. Phys.* (2000) 2:1305-1310.

Stender, H. et al. PNA for rapid microbiology; *J. Microbiological Methods.* (2002) 48:1-17.

Stork, M. et al. Energy Transfer in Mixtures of Water-Soluble Oligomers: Effect of Charge, Aggregation, and Surfactant Complexation; *Adv. Mater.* (2002) 14:5:361-368.

Su, X et al. Au nanoparticle- and sliver-enhancement reaction-amplified mIcrogravimetric biosensor, *Chem. Commun.* (2001) 755-756.

Sullenger, B.A. and Gilboa, E. Emerging clinical applications of RNA; *Nature.* (2002) 418:252-258.

Takakusa, H. et al. Design and Synthesis of an Enzyme-Cleavable Sensor Molecule for Phosphodiesterase Activity Based on Fluorescence Resonance Energy Transfer; *J. Am. Chem. Soc.* (2002) 124:8:1653-1657.

Tamilarasu, N. et al. A New strategy for Site-Spedfic Protein Modification: Analysis of a Tat Peptide-TAR RNA Interaction; *Bioconjugate Chem.* (2001) 12:2:135-138.

Tang, M.X. and Szoka, F.C. The influence of polymer structure on the interactions of cationic polymers with DNA and morphology of the resulting complexes; *Gene Ther.* (1997) 4:823-832.

Demers, L.M. et al. Thermal Desorption: J. Am. Chem. Soc. (2002) 124; 11248-11249.

Taton, T.A. et al. ScanometrIc DNA Array Detection with Nanoparticle Probes; *Science.* (2000) 289:1757-1760.

Taton, T.A. et al. Two-Color Labeling of Oligonucleotide Arrays via Size-Selective Scattering of Nanoparticle Probes; *J. Am. Chem. Soc.* (2001) 123:5164-5165.

Tomac, S. et al. Ionic Effects on the Stability and Conformation of Peptide Nucleic Acid Complexes; *J. Am. Chem. Soc.* (1996) 118:5544-5552.

Traser, S. et al. Syntheses and solution properties of water-soluble poly(p-phenylene)s bearing oligo(ethylene oxide) and trialkylamino side groups; *e-Polymers.* (2002) 32:1-39.

Umek, R.M. et al. Electronic Detection of Nucleic Adds—A Versatile Platform for Molecular Diagnostics; *J. Mol. Diag.* (2001) 3:2:74-84.

Vaishnav, Y.N. and Wong-Staal, F. The Biochemistry of Aids; *Ann. Rev. Biochem.* (1991) 60:577-630.

Varani, G. RNA-Protein Intermolecular Recognition; *Acc. Chem. Res.* (1997) 30:5:189-195.

Vinogradov, S.V. et al. Self-Assembly of Polyamine-Polyethylene glycol) Copolymers with Phosphorothloate Oligonucleotides; *Bloconfugate Chem.* (1998) 9:805-812.

Wang, J. et al. Photoluminescence of Water-Soluble Conjugated Polymers: Origin of Enhanced Quenching by Charge Transfer; *Macromolecules.* (2000) 33:5153-5158.

Wang, J. et al. DNA Electrochemical Biosensor for the Detection of Short DNA Sequences Related to the Human Immunodeficiency Virus; *Anal. Chem.* (1996) 68:15:2629-2634.

Isola, N.R. et al. Surface-Enhanced Raman Gene Probe for HIV Detection; *Anal. Chem.* (1998) 70:1352-1356.

Wang, J. Survey and Summary From DNA biosensors to gene chips; *Nucleic Acid Res.* (2000) 28:16:3011-3016.

Wang, J. et al. Dendritic Nucleic Acid Probes for DNA Biosensors; *J. Am. Chem. Soc.* (1998) 120:8281-8282.

Wang, J. et al. Synthesis of AB(BA), ABA and BAB Block Copolyrners of *tert*-Butyl Methacrylate (A) and Ethylene Oxide (B); *J. Polym. Sci., Part A: Polym. Chem.* (1992) 30:2251-2261.

Wang, Y. et al. Inte raction of DNA with Cationic Micelles: Effects of Micelle Surface Charge Density, Micelle Shape, and Ionic Strength on Complexation and DNA Collapse; *Langmuir.* (2001)17:1670-1673.

Waring, M. J. Complex Formation between Ethidium Bromide and Nucleic Acids; *J. Mol. Biol.* (1965) 13:269-282.

Weeks, K.M. et al. Fragments of the HIV-1 Tat Protein Specifically Bind TAR RNA; *Science.* (1990) 249:1281-1285.

Whitcombe, D. et al. Detection of PCR products using self-probing amplicons and fluorescence; *Nat. Biotechnol.* (1999) 17:804-807.

Wolfert, M.A. et al. Polyelectrolyte Vectors for Gene Delivery: Influence of Cationic Polymer on Biophysical Properties of Complexes Formed with DNA; *Bioconjugate Chem.* (1999) 10:993-1004.

Wyman, T.B. et al. Design, Synthesis, and Characterization of a Cationic Peptide that Binds to Nucleic Acids and Permeabilizes Bilayers; *Biochemistry.* (1997) 36:3008-3017.

Xu, X.H. and Bard, A.J. Immobilization and Hybridization of DNA on an Aluminum(II) Alkanebisphosphonate Thin Film with Electrogenerated Chemiluminescent Detection; *J. Am. Chem. Soc.* (1995) 117:2627-2631.

Yang, J.S. and Swager, T.M. Fluorescent Porous Polymer Films as TNT Chemosensors: Electronic and Structural Effects; *J. Am. Chem. Soc.* (1998) 120:11864-11873.

Junhui, Z. et al. DNA Based Biosensors; *Biotechnol. Adv.* (1997). 15:43-58.

U.S. Appl. No. 60/202,647, filed May 8, 2000, Whitten.
U.S. Appl. No. 60/226,902, filed Aug. 23, 2000, Whitten.
U.S. Appl. No. 60/230,186, filed Sep. 1, 2000, Philips.
U.S. Appl. No. 60/237,000, filed Sep. 29, 2000, Bruchez.
U.S. Appl. No. 60/240,216, filed Oct. 13, 2000, Bruchez.
U.S. Appl. No. 60/276,090, filed Mar. 16, 2001, Jones.
U.S. Appl. No. 60/314,094, filed Aug. 23, 2001, Burdick.
U.S. Appl. No. 60/314,101, filed Aug. 23, 2001, Whitten.

Wang et al., "Size-Specific Interactions Between Single- and Double-Stranded Oligonucleotides and Cationic Water-Soluble Oligofluorenes", Adv. Funct. Mater., Jun. 2003, 13(6), 463-467.

Chen et al., "Tuning the Properties of Conjugated Polyelectrolytes through Surfactant Complexation", J. Am. Chem. Soc., 2000, 122, 9302-9303.

Gaylord et al., "Water-Soluble Conjugated Oligomers: Effect of Chain Length and Aggregation on Photoluminescene-Quenching Efficiencies", J. Am. Chem. Soc., 2001, 123, 6417-6418.

Hong et al., "Water-Soluble Oligmer Dimers Based on Paracyclophane: A New optical Platform for Fluorescent Sensor Applications", J. Am. Chem. Soc., 2002, 124, 11868-11869.

Gaylord et al., "DNA Hybridization Detection with Water-Soluble Conjugated Polymers and Chromophore-Labeled Single-Stranded DNA", J. Am; Chem. Soc., 2003, 125, 896-900.

Zhou et al., "Fluorescent Chemosensors Based on Energy Migration in Conjugated Polymers: The Molecular Wire Approach to Increased Sensitivity", J. Am. Chem. Soc., 1995, 117, 12593-12602.

Zhou et al., "Methodology for Enhancing the Sensitivity of Fluorescent Chemosensors: Energy Migration in Conjugated Polymers", J. Am. Chem. Soc., 1995, 117, 7017-7018.

Hawkins et al., "Incorporation of a fluorescent guanosine analog Into oligonucleotides and its application to a real time assay for the HIV-1 integrase 3'-processing reaction", Nucleic Acids Research, 1995, 23(15), 2872-2880.

Cardullo et al., "Detection of Nucleic Acid Hybridization by Nonradiative Fluorescence Resonance Energy Transfer", Proc. Natl. Acad. Sci. USA, Dec. 1998, 85, 8790-8794.

Gallot et al., "Poly(L-lysine) containing azobenzene units in the side chains: influence of the degree of substitution on liquid crystalline structure and thermotropic behaviour", Liquid Crystals, 1997, 23(1), 137-146.

Wang et al., "Biosensors from conjugated polyelectrolyte complexes", PNAS, Jan. 2002, 99(1), 49-53.

Liu et al., "Methods for strand-specific DNA detection with cationic conjugation polymers suitable for incorporation into DNA chips and microarrays", PNAS Early Edition, Dec. 2004, p. 1-5.

Vehse et al., "Light Amplification by Optical Excitation of a Chemical Defect in a Conjugated Polymer", Adv. Mater., Jun. 2004, 16(12), 1001-1004.

Liu et al., "Shape-Adapable Water-Soluble Conjugated Polymers", J. Am. Cham. Soc., 2003, 125, 13306-13307.

Liu et al., "Interpolyelectrolyte Complexes of Conjugated Copolymers and DNA: Platforms for Multicolor Biosensors", J. Am. Chem. Soc., 2004, 126, 1942-1943.

Huang et al., "High-Efficiency, Evironment-Friendly Electroluminescent Polymers with Stable High Work Function Metal as a Cathode: Green- and Yellow-Emitting Conjugated Polyfluorene Polyelectrolytes and Their Neutral Precursors", J. Am. Chem. Soc., 2004, 126, 9845-9853.

Service, "DNA Analysis: Microchip Arrays Put DNA on the Spot", The American Association for the Advancement of Science, Oct. 1998, 282(5388), 396-399.

Southern, "DNA chips: analysing sequence by hybridization to oligonucleotides on a large scale", TIG, Mar. 1996, 12(3), 110-115.

Epstein et al., "Microarray technology—enhanced versatility, persistent challenge", Current Opinion in Biotechnology, 2000, 11, 36-41.

Heeger et al., "Making Sense of polymer-based biosensors", PNAS, Oct. 1999, 96(22), 12219-12221.

Patel et al., "Energy transfer analysis of Fos-Jun dimerization and DNA binding", Proc. Natl. Sci. USA, Jul. 2994, 91, 7360-7364.

Lohse et al., "Fluorescein-Conjugated Lysine Monomers for Solid Phase Synthesis of Fluorescents Peptides and PNA Oligomers", Bioconjugate Chem., 1997, 8, 503-509.

Smith et al., "The synthesis of oligonucleotides containing an aliphatic amino group at the 5' terminus: synthesis of fluorescent DNA primers for use in DNA sequence analysis", Nucleic Acids Research, 1985, 13(7) 2399-2412.

Wintermeyer et al., "Fluorescent Derivatives of Yeast tRNA(TM)", Eur. J. Biochem., 1979, 98, 465-475.

Lipshutz et al., "High density synthetic oligonucleotide arrays", Nature Genetics Supplement, Jan. 1999, 21, 20-24.

Nilsson et al., "Chip solution detection of DNA hybridization using a luminescent zwitterionic polythiophene derivative", Nature Materials, Jun. 2003, 2, 419-424 (Supplementary Information pp. 1-2).

Dore et al., "Fluorescent Polymeric Transducer for the Rapid, Simple, and Specific Detection of Nucleic Acids at the Zeptomole Level", J. Am. Chem. Soc., 2004, 126, 4240-4244.

Ranade et al., "High-Throughput Genotyping with Single Nucleotide Polymorphisms", Genone Research, 2001, 11, 1262-1268.

Schork et al., "Single nucleotide polymorphisms and the furture if genetic epidemiology", Clin. Genet., 2000, 58, 250-264.

Wang et al., "Optically Amplified RNA-Protein Detection Methods Using Light-Harvesting Conjugated Polymers", Adv. Mater., Sep. 2003, 15(17), 1425-1428.

Liu et al., "Homogeneuos Fluorescents-Based DNA Detection with Water-Soluble Conjugated Polymers", Chem. Mater., 2004, 16, 4467-4476.

Wolcott, "Advances in Nucleic Acid-Based Detection Methods", Clinical Microbiology Reviews, Oct. 1992, 5(4), 370-386.

Umek et al., "Electronic Detection of Nucleic Acids, A Versatile Platform for Molecular Diagnostics", Journal of Molecular Diagnostics, May 2001, 3(2), 74-84.

Stevens et al., "Exciton dissociation mechanisms in the polymeric semiconductors poly(9,9-dioctylfluorene) and poly(9,9-dioctylfluorene-co-benzothiadiazole)", Physical Review B, Apr. 2001, 63, 1-18.

Wang, "Survey and Summary From DNA biosensors to gene chips", Nucleic Acids Research, 2000, 28(16), 3011-3016.

Beier et al., "Versatile derivatisation of solid support media for covalent bonding on DNA-microchips", Nucleic Acids Research, 1999, 27(9), 1970-1977.
Weiler, "Hybridization based DNA screening on peptide nucleic acid (PNA) oligomer arrays", Nucleic Acids Research, 1997, Vol. 25, No. 14, pp. 2792-2799.
Bazan, "Characterisation of tectoRNA assembly with cationic conjugated polymers", JACS 126(13): 4076-4077, Apr. 7, 2004.
Huang, "Novel Electroluminescent Conjugated Polyelectrolytes based on Polyfluorene", Chemistry of Materials, Am. Chem. Soc. vol. 16(4): 708-716, 2004.
Ajayaghosh, "A novel approach toward low optical band gap polysquaraines", Organic Letters, vol. 3(16):2595-2598, 2001.
Gaylord, "SNP detection using peptide nucleic acid probes and conjugated polymers: Applications in neurodegenerative disease identification", PNAS, vol. 102(1):34-39, 2005.
Wang, "Fluorescein provides a resonance gate for FRET from conjugated polymers to DNA intercalated dyes", JACS 126(17):5446-5451, 2004.
Raymond, "Detection of target DNA using fluorescent cationic polymer and peptide nucleic acid probes on solid support," BMC Biotechnology vol. 5, Apr. 2005.
Brandt, "Peptide nucleic acids on microarrays and other biosensors", TIBS 22(12):617-622, Dec. 2004.
Wang, Solvent-dependent aggregation of a water-soluble poly(fluorene) controls energy trasfer to chromophore-labeled DNA, Chem. Comm., R. Soc. Chem., 2004, pp. 2508-2509.
Ajayaghosh, "A novel approach toward low optical band gap polysquaraines," Organic Letters, 3(16):2595-2598 (2001). *This reference was submitted in related U.S. Appl. No. 11/344,942. Please see this application for an original copy.
Bazan, "Characterisation of tectoRNA Assembly with cationic conjugated polymers," JACS, 126(13):4076-7044 (2004). *This reference was submitted in related U.S. Appl. No. 11/344,942. Please see this application for an original copy.
Brandt, "Peptide nucleic acids on microarrays and other biosensors," TIBS, 22(12):617-622 (2004), *This reference was submitted in related U.S. Appl. No. 11/344,942. Please see this application for an original copy.
Gaylord, "SNP detection using peptide nucleic acid probes and conjugated polymers: Applications in neurodegenerative disease identification," PNAS, 102(1):34-39 (2005).
Gaylord, "DNA detection using water-soluble conjugated polymers and peptide nucleic acid probes," PNAS, 99(17):182 (2002).
Huang, "Novel Electroluminescent Conjugated Polyelectrolytes based on Polyfluorene," Chemistry of Materials, Am. Chem. Soc., 16(4):708-716 (2004). *This reference was submitted in related U.S. Appl. No. 11/344,942. Please see this application for an original copy.
Liu et al., "Blue-light -emitting cationic water-soluble polyfluorene derivatives with tunable quaternization degree," Macromolecules, 35(13):4975-4982 (2002).
Raymond, "Detection of target DNA using fluoresence cationic polymer and peptide nucleic acid probes on solid support," BMD Biotechnology, vol. 5 (2005). *This reference was submitted in related U.S. Appl. No. 11/344,942. Please see this application for an original copy.
Stewart, "Chromophore-Labeled Dendrons as Light Harvesting Antennae," J. Am. Chem. Soc., 118 (18):4354-4360 (1996).
Wang, "Solvent-dependent aggregation of a water-soluble poly(fluorene) controls energy transfer to chromophore-labeled DNA," Chem. Comm, R. Soc. Chem., 2508-2509 (2004).
Wang, "Fluorescein provides a resonance gate for FRET from conjugated polymers to DNA intercalated dyes," JACS, 126(7):5446-5451 (2004). *This reference was submitted in related U.S. Appl. No. 11/344,942. Please see this application for an original copy.
Prosecution History for U.S. Appl. No. 10/600,286: All office actions and responses. Please see the paper copies or the Image File Wrapper (IFW) system of the USPTO for copies of the actions and responses.
Prosecution History for U.S. Appl. No. 11/746,055: All office actions and responses. Please see the paper copies or the Image File Wrapper (IFW) system of the USPTO for copies of the actions and responses.
Prosecution History for U.S. Appl. No. 10/779,412: All office actions and responses. Please see the paper copies or the Image File Wrapper (IFW) system of the USPTO for copies of the actions and responses.
Prosecution History for U.S. Appl. No. 10/666,333: All office actions and responses. Please see the paper copies or the Image File Wrapper (IFW) system of the USPTO for copies of the actions and responses.
Prosecution History for U.S. Appl. No. 10/648,945: All office actions and responses. Please see the paper copies or the Image File Wrapper (IFW) system of the USPTO for copies of the actions and responses.
Prosecution History for U.S. Appl. No. 11/329,861: All office actions and responses. Please see the paper copies or the Image File Wrapper (IFW) system of the USPTO for copies of the actions and responses.
Prosecution History for U.S. Appl. No. 11/329,495: All office actions and responses. Please see the paper copies or the Image File Wrapper (IFW) system of the USPTO for copies of the actions and responses.
Prosecution History for U.S. Appl. No. 11/344,942: All office actions and responses. Please see the paper copies or the Image File Wrapper (IFW) system of the USPTO for copies of the actions and responses.
Prosecution History for U.S. Appl. No. 11/868,870: All office actions and responses. Please see the paper copies or the Image File Wrapper (IFW) system of the USPTO for copies of the actions and responses.
International Search Report issued Apr. 14, 2004 in PCT/US2003/019678.
Office action issued Oct. 20, 2006 and response thereto filed May 6, 2007 in CN03819836.3.
Office action issued Sep. 25, 2008 and response thereto filed Feb. 25, 2009 in CN03819836.3.
Supplementary EP Search Report issued Sep. 27, 2007 in EP 03761235.5.
Examination Report issued Jul. 17, 2008 and response thereto filed Jan. 26, 2009 in EP 03761235.5.
First Office Action issued Mar. 17, 2009 in JP 2004-516105.
Examination Report issued Aug. 31, 2006 in NZ 537707.
Written Opinion issued Oct. 7, 2005 and response thereto filed Mar. 6, 2006 in SG 200407571-9.
Examination report issued Jun. 26, 2006 in SG 200407571-9.
International Search Report and Written Opinion issued Mary 12, 2005 in PCT/US2004/04286.
International Preliminary Report on Patentability issued Aug. 19, 2005 in PCT/US2004/04286.
First Office Action issued Apr. 13, 2007 in CN 200480009631.4.
Supplementary EP Search Report issued Sep. 27, 2007 in EP 04737272.7.
International Search Report and Written Opinion issued Dec. 16, 2005 in PCT/US2004/030605.
International Preliminary Report on Patentability issued Mar. 21, 2006 in PCT/US2004/030605.
Examination report issued Sep. 10, 2008 and response thereto filed Mar. 20, 2009 in EP 04821601.4
International Search Report issued Mar. 18, 2005 in PCT/US2003/026989.
First Office Action issued Apr. 28, 2005 and response thereto filed Nov. 13, 2006 in CN 03824651.1.
Decision on Rejection issued Jul. 6, 2007 in CN 03824651.1 and Request for Reexamination filed Oct. 18, 2007 in CN 03824651.1.
Prosecution History for U.S. Appl. No. 11/854,365: All office actions and responses. Please see the paper copies or the Image File Wrapper (IFW) system of the USPTO for copies of the actions and responses.
Supplementary European Search Report issued Sep. 20, 2007 in EP 03816297.
Official Action issued Jul. 17, 2008 and response thereto filed Jan. 21, 2009 in EP 03816297.
International Search Report and Written Opinion issued Dec. 12, 2006 in PCT/US2006/00928.
International Preliminary Report on Patentability issued Jul. 10, 2007 in PCT/US2006/00928.
International Search Report and Written Opinion issued Aug. 16, 2006 in PCT/US2006/00882.
International Preliminary Report on Patentability issued Jul. 10, 2007 in PCT/US2006/00882.
International Search Report and Written Opinion issued Sep. 11, 2006 in PCT/US2006/003498.

International Preliminary Report on Patentability issued Jul. 31, 2007 in PCT/US2006/003498.
Sun et al., "Application of cationic conjugated polymers in microarrays using label-free DNA targets," Nature Protocols, 2(9):1-4-(2007).
Examination Report issued Jan. 17, 2008 and response thereto filed Jul. 25, 2008 in EP 04737272.7.
Prosecution History for U.S. Appl. No. 11/561,893: All office actions and responses. Please see the paper copies or the Image File Wrapper (IFW) system of the USPTO for copies of the actions and responses.
Decision on Rejection issued Jul. 3, 2009 in CN 03819836.3.
First Office Action issued May 12, 2009 and response thereto filed Aug. 12, 2009 in JP 2004-570933.
U.S. Appl. No. 10/600,286, Mar. 13, 2006, Mail Restriction Requirement.
U.S. Appl. No. 10/600,286, Apr. 18, 2006, Response to Election/Restriction Filed.
U.S. Appl. No. 10/600,286, May 31, 2006, Mail Non-Final Rejection.
U.S. Appl. No. 10/600,286, Sep. 6, 2006, Response after Non-Final Rejection.
U.S. Appl. No. 10/600,286, Nov. 14, 2006, Mail Notice of Allowance.
PCT/US03/019678, Apr. 14, 2004, International Search Report.
CN 03819836.3, Oct. 20, 2006, First Office Action.
CN 03819836.3, May 6, 2007, Response to First Office Action.
CN 03819836.3, Sep. 25, 2008, Second Office Action.
CN 03819836.3, Feb. 25, 2009, Response to Second Office Action.
CN 03819836.3, Jul. 3, 2009, Decision on Rejection.
EP 03761235.5, Sep. 27, 2007, Supplementary EP search report.
EP 03761235.5, Jul. 17, 2008, Examination Report.
EP 03761235.5, Jan. 26, 2009, Response Filed.
JP 2004-516105, Mar. 17, 2009, First Office Action.
NZ537707, Aug. 31, 2006, Examination Report.
SG200407571-9, Oct. 7, 2005, Written Opinion.
SG200407571-9, Mar. 6, 2006, Response to Written Opinion.
SG200407571-9, Jun. 26, 2006, Examination Report.
U.S. Appl. No. 10/779,412, Jul. 10, 2006, Mail Restriction Requirement.
U.S. Appl. No. 10/779,412, Sep. 18, 2006, Response to Election/Restriction Filed.
U.S. Appl. No. 10/779,412, Jan. 16, 2007, Mail Non-Final Rejection.
U.S. Appl. No. 10/779,412, May 17, 2007, Response after Non-Final Rejection.
U.S. Appl. No. 10/779,412, Aug. 28, 2007, Response after Non-Final Rejection.
U.S. Appl. No. 10/779,412, Oct. 26, 2007, Mail Notice of Informal or Non-Responsive Amendment.
U.S. Appl. No. 10/779,412, Nov. 26, 2007, Response after Non-Final Rejection.
U.S. Appl. No. 10/779,412, Feb. 6, 2008, Mail Non-Final Rejection.
U.S. Appl. No. 10/779,412, Jul. 7, 2008, Response after Non-Final.
U.S. Appl. No. 10/779,412, Sep. 11, 2008, Mail Non-Final Rejection.
U.S. Appl. No. 10/779,412, Mar. 11, 2009, Notice of Appeal Filed.
PCT/US04/04286, May 12, 2005, International Search Report.
PCT/US04/04286, May 12, 2005, Written Opinion.
PCT/US04/04286, Aug. 19, 2005, International Preliminary Report on Patentability.
CN 200480009631.4, Apr. 13, 2007, First Office Action.
EP 04737272.7, Sep. 27, 2007, Supplementary EP Search Report.
EP 04737272.7, Jan. 17, 2008, Examination Report.
EP 04737272.7, Jul. 25, 2008, Response filed.
U.S. Appl. No. 10/666,333, Nov. 2, 2004, Mail Restriction Requirement.
U.S. Appl. No. 10/666,333, Jan. 7, 2005, Response to Election/Restriction Filed.
U.S. Appl. No. 10/666,333, Feb. 8, 2005, Mail Restriction Requirement.
U.S. Appl. No. 10/666,333, Mar. 14, 2005, Response to Election/Restriction Filed.
U.S. Appl. No. 10/666,333, May 12, 2005, Mail Non-Final Rejection.
U.S. Appl. No. 10/666,333, Oct. 14, 2005, Response after Non-Final Action.
U.S. Appl. No. 10/666,333, Nov. 9, 2005, Mail Final Rejection.
U.S. Appl. No. 10/666,333, Apr. 18, 2006, Amendment after Final Rejection.
U.S. Appl. No. 10/666,333, May 9, 2006, Mail Notice of Allowance.
PCT/US04/030605, Dec. 16, 2005, International Search Report.
PCT/US04/030605, Dec. 16, 2005, Written Opinion.
PCT/US04/030605, Mar. 21, 2006, International Preliminary Report on Patentability.
EP 04821601.4, Sep. 10, 2008, Examination Report.
EP 04821601.4, Mar. 20, 2009, Response Filed.
U.S. Appl. No. 10/648,945, Jun. 5, 2006, Mail Restriction Requirement.
U.S. Appl. No. 10/648,945, Sep. 11, 2006, Response to Election/Requirement.
U.S. Appl. No. 10/648,945, Nov. 14, 2006, Mail Non-Final Rejection.
U.S. Appl. No. 10/648,945, Feb. 23, 2007, Response after Non-Final Action.
U.S. Appl. No. 10/648,945, May 15, 2007, Mail Notice of Allowance.
U.S. Appl. No. 11/854,365, May 30, 2008, Mail Non-Final Rejection.
U.S. Appl. No. 11/854,365, Oct. 30, 2008, Response after Non-Final Rejection.
U.S. Appl. No. 11/854,365, Mar. 3, 2009, Mail Notice of Allowance.
PCT/US03/026989, Mar. 18, 2005, International Search Report.
CN 03824651.1, Apr. 28, 2006, First Office Action.
CN 03824651.1, Nov. 13, 2006, Response to First Office Action.
CN 03824651.1, Jul. 6, 2007, Decision on Rejection.
CN 03824651.1, Oct. 18, 2007, Request for Reexamination.
EP 03816297, Sep. 20, 2007, Supplementary European Search Report.
EP 03816297, Jul. 17, 2008, Official Action.
EP 03816297, Jan. 21, 2009, Response Filed.
JP 2004-570933, May 12, 2009, First Office Action.
JP 2004-570933, Aug. 12, 2009, Response to First Office Action.
PCT/US06/00928, Dec. 12, 2006, International Search Report.
PCT/US06/00928, Dec. 12, 2006, Written Opinion.
PCT/US06/00928, Jul. 10, 2007, International Preliminary Report on Patentability.
U.S. Appl. No. 11/329,495, Jan. 15, 2009, Restriction Requirement.
U.S. Appl. No. 11/329,495, Mar. 16, 2009, Response to Restriction Requirement.
U.S. Appl. No. 11/329,495, Jun. 18, 2009, Mail Non-Final Rejection.
PCT/US06/00882, Aug. 16, 2006, International Search Report.
PCT/US06/00882, Aug. 16, 2006, Written Opinion.
PCT/US06/00882, Jul. 10, 2007, International Preliminary Report on Patentability.
U.S. Appl. No. 11/329,861, Jun. 6, 2006, Mail Restriction Requirement.
U.S. Appl. No. 11/329,861, Aug. 8, 2007, Response to Election/Requirement.
U.S. Appl. No. 11/329,861, Nov. 26, 2007, Mail Non-Final Rejection.
U.S. Appl. No. 11/329,861, May 27, 2008, Response after Non-Final Rejection.
U.S. Appl. No. 11/329,861, Aug. 26, 2008, Mail Final Rejection.
U.S. Appl. No. 11/329,861, Jan. 27, 2009, Notice of Appeal Filed.
U.S. Appl. No. 11/334,942, Jan. 15, 2008, Mail Restriction Requirement.
U.S. Appl. No. 11/334,942, Apr. 15, 2008, Response to Election/Requirement.
U.S. Appl. No. 11/334,942, Jun. 9, 2008, Mail Non-Final Rejection.
U.S. Appl. No. 11/334,942, Oct. 9, 2008, Response after Non-Final Rejection.
U.S. Appl. No. 11/334,942, Dec. 31, 2008, Mail Final Rejection.
U.S. Appl. No. 11/334,942, May 13, 2009, Response to Final Rejection.
U.S. Appl. No. 11/334,942, May 26, 2009, Mail Notice of Allowance.
PCT/US06/003498, Sep. 11, 2006, International Search Report.
PCT/US06/003498, Sep. 11, 2006, Written Opinion.
PCT/US06/003498, Jul. 31, 2007, International Preliminary Report on Patentability.

* cited by examiner (A)

(B)

(A)

(B)

METHODS AND ARTICLES FOR STRAND-SPECIFIC POLYNUCLEOTIDE DETECTION WITH CATIONIC MULTICHROMOPHORES

STATEMENT REGARDING FEDERALLY SPONSORED RESEARCH

This invention was made with Government support under Grant Nos. 0343312 and GM62958-01 awarded by the National Science Foundation and the National Institutes of Health. The U.S. Government may have limited rights in this invention.

TECHNICAL FIELD

This invention relates to methods, articles and compositions for the detection and analysis of biomolecules in a sample. The invention further relates to conjugated polymers and methods, articles and compositions employing them as described herein.

BACKGROUND OF THE INVENTION

Methods for the detection of biomolecules such as nucleic acids are highly significant not only in identifying specific targets, but also in understanding their basic function. Hybridization probe technologies in particular continue to be one of the most essential elements in the study of gene-related biomolecules.[1,2,3] They are useful for a variety of both commercial and scientific applications, including the identification of genetic mutations or single nucleotide polymorphisms (SNP's), medical diagnostics, gene delivery, assessment of gene expression, and drug discovery.[4,5,6,7] Heterogeneous formats for performing such hybridization probe assays have become increasingly common and powerful with the advancement of gene chip and DNA microarray technologies.[8,9,10,11] Such systems allow for high throughput screening of hundreds to thousands of genes in a single experiment.

There is a continuing need in the art for methods of detecting and analyzing particular biomolecules in a sample, and for compositions and articles of manufacture useful in such methods. There is a need in the art for novel CCPs, for methods of making and using them, and for compositions and articles of manufacture comprising such compounds.

DETAILED DESCRIPTION OF THE INVENTION

Homogeneous DNA assays with increased sensitivity, relative to small molecular counterparts, have recently appeared that take advantage of the optical amplification afforded by conjugated polymers.[12] The emission intensities of acceptor chromophores on hybridization probes are magnified, relative to direct excitation, when the absorption coefficient of the polymer is large and the fluorescence resonance energy transfer (FRET) from the polymer to the acceptor is efficient.[13] Conjugated polymers offer other transduction mechanisms, for instance their optical properties can be modified upon complexation with double stranded or single stranded DNA.[14]

Figure 1:
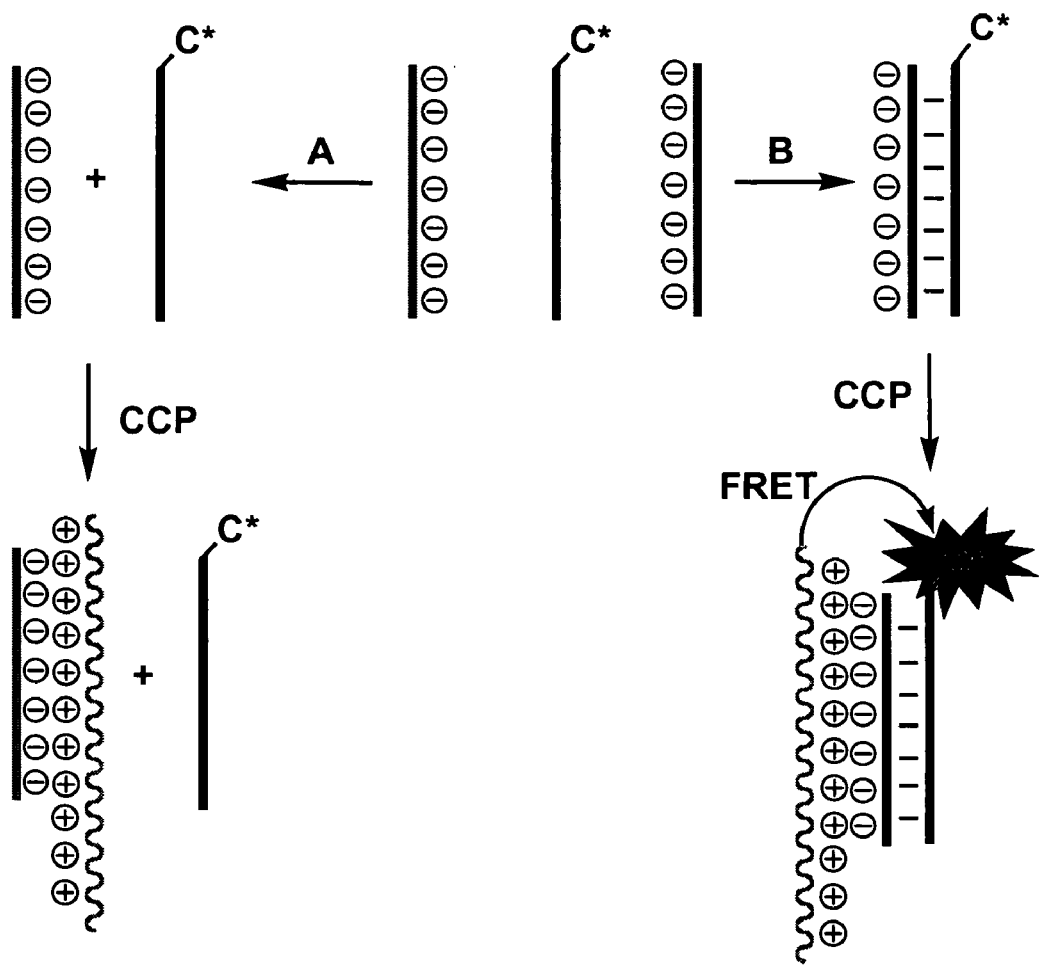
FIG. 1. Use of cationic conjugated polymers (CCPs) for the detection of PNA/DNA hybridization. The CCP is shown in orange, the PNA-C* in black, the non complementary ssDNA in green and the complementary ssDNA in red.

One successful DNA sensing method involves the use of labeled peptide nucleic acids (PNAs) and cationic conjugated polymers (CCPs). The assay, shown in FIG. 1, takes advantage of electrostatic interactions typical of oppositely charged polyelectrolytes.[15] There are three components in the assay: a CCP (shown in orange), a PNA-C* (shown in black), where C* is a reporter fluorophore, and the negatively charged target single stranded DNA (ssDNA), which may be complementary (in red) or non-complementary (in green) to the PNA sequence. The PNA-C* and the ssDNA are first treated according to hybridization protocols and the CCP is added to the resulting solution. If the ssDNA does not hybridize, one encounters situation A in FIG. 1, where the ssDNA and the CCP are brought together by non specific electrostatic forces. The PNA-C* is not incorporated into the electrostatic complex. Situation B shows that when the PNA-C* and the complementary ssDNA hybridize, the CCP binds to the duplex structure. If the optical properties of the CCP and the C* are optimized, then selective excitation of the CCP results in very efficient FRET to C*. One can therefore monitor the presence of specific ssDNA sequences by monitoring the C* emission or the CCP to C* emission ratio. Although FIG. 1 is specific to PNA/DNA interactions, other similar assays have appeared that incorporate peptide/RNA, DNA/DNA and RNA/RNA recognition pairs.[16]

A strand-specific polynucleotide sensing method is described based on surface bound peptide nucleic acids (PNAs) and water-soluble cationic conjugated polymers (CCPs). The main transduction mechanism operates by taking advantage of the net increase in negative charge at the PNA surface, which occurs upon ssDNA hybridization. Electrostatic forces cause the oppositely charged CCP to bind selectively to the "complementary" surfaces. This approach circumvents the current need to label the probe or target strands. The polymer used in these assays is poly[9,9'-bis(6"-N,N,N-trimethylammonium)hexyl)fluorene-co-alt-4,7-(2,1, 3-benzothiadiazole)dibromide] (PFBT), which was specifically designed and synthesized to be compatible with excitation sources used in commonly used DNA microarray readers. Furthermore, the utility of PFBT has been demonstrated in homogenous and solid-state assays that involve fluorescence resonance energy transfer (FRET) to a reporter dye (Cy5) and that can benefit from the light harvesting properties observed in water soluble conjugated polymers.

The inventions described herein are useful for any assay in which a sample can be interrogated regarding a target biomolecule. Typical assays involve determining the presence of the target biomolecule in the sample or its relative amount, or the assays may be quantitative or semi-quantitative.

The methods can be performed on a substrate. The assay can be performed in an array format on a substrate, which can be a sensor. These substrates may be surfaces of glass, silicon, paper, plastic, or the surfaces of optoelectronic semiconductors (such as, but not confined to, indium-doped gallium nitride or polyanilines, etc.) employed as optoelectronic transducers. The location of a given sensor polynucleotide may be known or determinable in an array format, and the array format may be microaddressable or nano addressable.

The methods of the invention can all be performed in multiplex formats. A plurality of different sensor polynucleotides can be used to detect corresponding different target polynucleotides in a sample through the use of different signaling chromophores conjugated to the respective sensor polynucleotides or through the use of localization of particular sensor polynucleotides to determinable regions of the substrate. Multiplex methods are provided employing 2, 3, 4, 5, 10, 15, 20, 25, 50, 100, 200, 400 or more different sensors which can be used simultaneously to assay for corresponding different target polynucleotides.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a target polynucleotide" includes a plurality of target polynucleotides, reference to "a sensor polynucleotide" includes a plurality of sensor polynucleotides, and the like. Additionally, use of specific plural references, such as "two," "three," etc., read on larger numbers of the same subject less the context clearly dictates otherwise.

Terms such as "connected," "attached," "conjugated" and "linked" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

DEFINITIONS

In describing the present invention, the following terms will be employed, and are intended to be defined as indicated below.

"Alkyl" refers to a branched, unbranched or cyclic saturated hydrocarbon group of 1 to 24 carbon atoms optionally substituted at one or more positions, and includes polycyclic compounds. Examples of alkyl groups include optionally substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, eicosyl, tetracosyl and the like, as well as cycloalkyl groups such as cyclopropyl, cyclobutyl, cyclopentyl, cyclohexyl, cycloheptyl, cyclooctyl, adamantyl, and norbornyl. The term "lower alkyl" refers to an alkyl group of 1 to 6 carbon atoms, preferably 1 to 4 carbon atoms. Exemplary substituents on substituted alkyl groups include hydroxyl, cyano, alkoxy, =O, =S, —$NO_2$, halogen, haloalkyl, heteroalkyl, carboxyalkyl, amine, amide, thioether and —SH.

"Alkoxy" refers to an "-Oalkyl" group, where alkyl is as defined above. A "lower alkoxy" group intends an alkoxy group containing one to six, more preferably one to four, carbon atoms.

"Alkenyl" refers to a branched, unbranched or cyclic hydrocarbon group of 2 to 24 carbon atoms containing at least one carbon-carbon double bond optionally substituted at one or more positions. Examples of alkenyl groups include ethenyl, 1-propenyl, 2-propenyl(allyl), 1-methylvinyl, cyclopropenyl, 1-butenyl, 2-butenyl, isobutenyl, 1,4-butadienyl, cyclobutenyl, 1-methylbut-2-enyl, 2-methylbut-2-en-4-yl, prenyl, pent-1-enyl, pent-3-enyl, 1,1-dimethylallyl, cyclopentenyl, hex-2-enyl, 1-methyl-1-ethylallyl, cyclohexenyl, heptenyl, cycloheptenyl, octenyl, cyclooctenyl, decenyl, tetradecenyl, hexadecenyl, eicosenyl, tetracosenyl and the like. Preferred alkenyl groups herein contain 2 to 12 carbon atoms. The term "lower alkenyl" intends an alkenyl group of 2 to 6 carbon atoms, preferably 2 to 4 carbon atoms. The term "cycloalkenyl" intends a cyclic alkenyl group of 3 to 8, preferably 5 or 6, carbon atoms. Exemplary substituents on substituted alkenyl groups include hydroxyl, cyano, alkoxy, =O, =S, —$NO_2$, halogen, haloalkyl, heteroalkyl, amine, thioether and —SH.

"Alkenyloxy" refers to an "-Oalkenyl" group, wherein alkenyl is as defined above.

"Alkylaryl" refers to an alkyl group that is covalently joined to an aryl group. Preferably, the alkyl is a lower alkyl. Exemplary alkylaryl groups include benzyl, phenethyl, phenopropyl, 1-benzylethyl, phenobutyl, 2-benzylpropyl and the like.

"Alkylaryloxy" refers to an "-Oalkylaryl" group, where alkylaryl is as defined above.

"Alkynyl" refers to a branched or unbranched hydrocarbon group of 2 to 24 carbon atoms containing at least one —C≡C— triple bond, optionally substituted at one or more positions. Examples of alkynyl groups include ethynyl, n-propynyl, isopropynyl, propargyl, but-2-ynyl, 3-methylbut-1-ynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— triple bond. Exemplary substituents on substituted alkynyl groups include hydroxyl, cyano, alkoxy, =O, =S, —$NO_2$, halogen, haloalkyl, heteroalkyl, amine, thioether and —SH.

"Amide" refers to —C(O)NR'R", where R' and R" are independently selected from hydrogen, alkyl, aryl, and alkylaryl.

"Amine" refers to an —N(R')R" group, where R' and R" are independently selected from hydrogen, alkyl, aryl, and alkylaryl.

"Aryl" refers to an aromatic group that has at least one ring having a conjugated pi electron system and includes carbocyclic, heterocyclic, bridged and/or polycyclic aryl groups, and can be optionally substituted at one or more positions. Typical aryl groups contain 1 to 5 aromatic rings, which may be fused and/or linked. Exemplary aryl groups include phenyl, furanyl, azolyl, thiofuranyl, pyridyl, pyrimidyl, pyrazinyl, triazinyl, biphenyl, indenyl, benzofuranyl, indolyl, naphthyl, quinolinyl, isoquinolinyl, quinazolinyl, pyridopyridinyl, pyrrolopyridinyl, purinyl, tetralinyl and the like. Exemplary substituents on optionally substituted aryl groups include alkyl, alkoxy, alkylcarboxy, alkenyl, alkenyloxy, alkenylcarboxy, aryl, aryloxy, alkylaryl, alkylaryloxy, fused saturated or unsaturated optionally substituted rings, halogen, haloalkyl, heteroalkyl, —S(O)R, sulfonyl, —$SO_3$R, —SR, —$NO_2$, —NRR', —OH, —CN, —C(O)R, —OC(O)R, —NHC(O)R, —$(CH_2)_n CO_2 R$ or —$(CH_2)_n CONRR'$ where n is 0-4, and wherein R and R' are independently H, alkyl, aryl or alkylaryl.

"Aryloxy" refers to an "-Oaryl" group, where aryl is as defined above.

"Carbocyclic" refers to an optionally substituted compound containing at least one ring and wherein all ring atoms are carbon, and can be saturated or unsaturated.

"Carbocyclic aryl" refers to an optionally substituted aryl group wherein the ring atoms are carbon.

"Halo" or "halogen" refers to fluoro, chloro, bromo or iodo. "Halide" refers to the anionic form of the halogens.

"Haloalkyl" refers to an alkyl group substituted at one or more positions with a halogen, and includes alkyl groups substituted with only one type of halogen atom as well as alkyl groups substituted with a mixture of different types of halogen atoms. Exemplary haloalkyl groups include trihalomethyl groups, for example trifluoromethyl.

"Heteroalkyl" refers to an alkyl group wherein one or more carbon atoms and associated hydrogen atom(s) are replaced by an optionally substituted heteroatom, and includes alkyl groups substituted with only one type of heteroatom as well as alkyl groups substituted with a mixture of different types of heteroatoms. Heteroatoms include oxygen, sulfur, and nitrogen. As used herein, nitrogen heteroatoms and sulfur heteroatoms include any oxidized form of nitrogen and sulfur, and any form of nitrogen having four covalent bonds including protonated forms. An optionally substituted heteroatom refers to replacement of one or more hydrogens attached to a nitrogen atom with alkyl, aryl, alkylaryl or hydroxyl.

"Heterocyclic" refers to a compound containing at least one saturated or unsaturated ring having at least one heteroatom and optionally substituted at one or more positions. Typical heterocyclic groups contain 1 to 5 rings, which may be fused and/or linked, where the rings each contain five or six atoms. Examples of heterocyclic groups include piperidinyl, morpholinyl and pyrrolidinyl. Exemplary substituents for optionally substituted heterocyclic groups are as for alkyl and aryl at ring carbons and as for heteroalkyl at heteroatoms.

"Heterocyclic aryl" refers to an aryl group having at least 1 heteroatom in at least one aromatic ring. Exemplary heterocyclic aryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl and the like.

"Hydrocarbyl" refers to hydrocarbyl substituents containing 1 to about 20 carbon atoms, including branched, unbranched and cyclic species as well as saturated and unsaturated species, for example alkyl groups, alkylidenyl groups, alkenyl groups, alkylaryl groups, aryl groups, and the like. The term "lower hydrocarbyl" intends a hydrocarbyl group of one to six carbon atoms, preferably one to four carbon atoms.

A "substituent" refers to a group that replaces one or more hydrogens attached to a carbon or nitrogen. Exemplary substituents include alkyl, alkylidenyl, alkylcarboxy, alkoxy, alkenyl, alkenylcarboxy, alkenyloxy, aryl, aryloxy, alkylaryl, alkylaryloxy, —OH, amide, carboxamide, carboxy, sulfonyl, =O, =S, —NO$_2$, halogen, haloalkyl, fused saturated or unsaturated optionally substituted rings, —S(O)R, —SO$_3$R, —SR, —NRR', —OH, —CN, —C(O)R, —OC(O)R, —NHC(O)R, —(CH2)$_n$CO$_2$R or —(CH2)$_n$CONRR' where n is 0-4, and wherein R and R' are independently H, alkyl, aryl or alkylaryl. Substituents also include replacement of a carbon atom and one or more associated hydrogen atoms with an optionally substituted heteroatom.

"Sulfonyl" refers to —S(O)$_2$R, where R is alkyl, aryl, —C(CN)=C-aryl, —CH$_2$CN, alkylaryl, or amine.

"Thioamide" refers to —C(S)NR'R", where R' and R" are independently selected from hydrogen, alkyl, aryl, and alkylaryl.

"Thioether" refers to —SR, where R is alkyl, aryl, or alkylaryl.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

Whether modified or unmodified, in some embodiments the target nucleotide must have a polyanionic backbone, preferably a sugar-phosphate background, of sufficient negative charge to electrostatically interact with the polycationic multichromophore in the methods described herein, although other forces may additionally participate in the interaction. The sensor polynucleotide is exemplified as a peptide nucleic acid, although other polynucleotides which minimally interact with the multichromophore in the absence of target can be used. Suitable hybridization conditions for a given assay format can be determined by one of skill in the art; nonlimiting parameters which may be adjusted include concentrations of assay components, pH, salts used and their concentration, ionic strength, temperature, etc.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing a phosphate or other polyanionic backbone, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-aminopyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al.

Other nonnatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

"Complementary" or "substantially complementary" refers to the ability to hybridize or base pair between nucleotides or nucleic acids, such as, for instance, between a sensor polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203 (1984).

"Preferential binding" or "preferential hybridization" refers to the increased propensity of one polynucleotide or PNA to bind to its complement in a sample as compared to a noncomplementary polymer in the sample.

Hybridization conditions will typically include salt concentrations of less than about 1M, more usually less than about 500 mM and preferably less than about 200 mM. In the case of hybridization between a peptide nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

"Optional" or "optionally" means that the subsequently described event or circumstance may or may not occur, and that the description includes instances where the event or circumstance occurs and instances in which it does not.

The Sample

The portion of the sample comprising or suspected of comprising the target biomolecule can be any source of biological material which comprises biomolecule that can be obtained from a living organism directly or indirectly, including cells, tissue or fluid, and the deposits left by that organism, including viruses, mycoplasma, and fossils. In some embodiments, the target biomolecule comprises a polynucleotide. The sample may comprise a target polynucleotide prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the target polynucleotide or a surrogate therefor. A negative control sample can also be used which, although not expected to contain the target polynucleotide, is suspected of containing it (via contamination of one or more of the reagents) or another component capable of producing a false positive, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

The Target Biomolecule

A target biomolecule (e.g., a polysaccharide, a polynucleotide, a peptide, a protein, etc.) is employed that can bind to a sensor biomolecule. The target may also interact at least in part electrostatically with a polycationic multichromophore, which may be a conjugated polymer. In some embodiments, a target polynucleotide is employed, and may be complementary to a sensor polynucleotide.

In embodiments where the target biomolecule is a polynucleotide, the target polynucleotide can be single-stranded, double-stranded, or higher order, and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide. Conversely, where the target polynucleotide is too concentrated for the particular assay, the target polynucleotide may be diluted.

Following sample collection and optional nucleic acid extraction, the nucleic acid portion of the sample comprising the target polynucleotide can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target polynucleotide. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target polynucleotide is single-stranded, the first cycle of amplification forms a primer extension product complementary to the target polynucleotide. If the target polynucleotide is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H⁻ MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

Amplified target polynucleotides may be subjected to post amplification treatments. For example, in some cases, it may be desirable to fragment the target polynucleotide prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow the sensor polynucleotide to hybridize to the amplification product during at least part of an amplification cycle. When the assay is performed in this manner, real-time detection of this hybridization event can take place by monitoring for light emission from the polycationic multichromophore in the vicinity of the sensor during amplification.

The Polycationic Multichromophore

Light harvesting multichromophore systems can efficiently transfer energy to nearby luminescent species. Mechanisms for energy transfer include, for example, resonant energy transfer (Förster (or fluorescence) resonance energy transfer, FRET), quantum charge exchange (Dexter energy transfer) and the like. Typically, however, these energy transfer mechanisms are relatively short range, and close proximity of the light harvesting multichromophore system to the signaling chromophore is required for efficient energy transfer. Amplification of the emission can occur when the number of individual chromophores in the light harvesting multichromophore system is large; emission from a fluorophore can be more intense when the incident light (the "pump light") is at a wavelength which is absorbed by the light harvesting multichromophore system and transferred to the fluorophore than when the fluorophore is directly excited by the pump light.

The multichromophores used in the present invention are polycationic so that they can interact with a biomolecule comprising multiple anionic groups, e.g. polysaccharides, polynucleotides, peptides, proteins, etc. In some embodiments, the multichromophore can interact with a target polynucleotide electrostatically and thereby bring a signaling chromophore on an uncharged sensor polynucleotide into energy-receiving proximity by virtue of hybridization between the sensor polynucleotide and the target polynucleotide. Any polycationic multichromophore that can absorb light and preferably emit or transfer energy can be used in the methods described. Exemplary multichromophores that can be used include conjugated polymers, saturated polymers or dendrimers incorporating multiple chromophores in any viable manner, and semiconductor nanocrystals (SCNCs). The conjugated polymers, saturated polymers and dendrimers can be prepared to incorporate multiple cationic species or can be derivatized to render them polycationic after synthesis; semiconductor nanocrystals can be rendered polycationic by addition of cationic species to their surface. In some embodiments, the polycationic multichromophore is not detected by its ability to transfer energy when excited, and thus methods involving such detection schemes do not require the multichromophore to emit or transfer energy.

In some embodiments, the multichromophore is a conjugated polymer (CP). More preferably, the CP is one that comprises "low bandgap repeat units" of a type and in an amount that contribute an absorption to the polymer in the range of about 450 nm to about 1000 nm. The low bandgap repeat units may or may not exhibit such an absorption prior to polymerization, but does introduce that absorption when incorporated into the conjugated polymer. Such absorption characteristics allow the polymer to be excited at wavelengths that produce less background fluorescence in a variety of settings, including in analyzing biological samples and imaging and/or detecting molecules. Shifting the absorbance of the CP to a lower energy and longer wavelength thus allows for more sensitive and robust methods. Additionally, many commercially available instruments incorporate imaging components that operate at such wavelengths at least in part to avoid such issues. For example, thermal cyclers that perform real-time detection during amplification reactions and microarray readers are available which operate in this region. Providing polymers that absorb in this region allows for the adaptation of detection methods to such formats, and also allows entirely new methods to be performed.

Incorporation of repeat units that decrease the band gap can produce conjugated polymers with such characteristics. Exemplary optionally substituted species which result in polymers that absorb light at such wavelengths include 2,1, 3-benzothiadiazole, benzoselenadiazole, benzotellurodiazole, naphthoselenadiazole, 4,7-di(thien-2-yl)-2,1,3-benzothiadiazole, squaraine dyes, quinoxalines, low bandgap commercial dyes, olefins, and cyano-substituted olefins and isomers thereof.

For example, 2,7-carbazolene-vinylene conjugated polymers have been described with peak absorptions ranging from about 455-485 nm (Morin et al., Chem. Mater. 2004, vol. 16, No. 23, pages 4619-4626). Polymers can be prepared incorporating benzoselenadiazole with absorption maxima at 485 nm. Similarly, polymers incorporating naphthoselenadiazole are known with absorption maxima at 550 nm. Polymers incorporating 4,7-di(thien-2-yl)-2,1,3-benzothiadiazole are known with absorption maxima at about 515 nm. Polymers incorporating cyanovinylenes are known with peak absorptions in this region, for example from 372-537 nm, and exhibiting absorption above 700 nm (PFR(1-4)-S, Macromolecules, Vol. 37, No. 14, pages 5265-5273). Preparation of polymers incorporating monomers that provide absorption in the spectral region up to 1000 nm has been described (Ajayaghosh, A., et al., Chem. Soc. Rev., 2003, 32, 181; A. Ajayagosh and J. Eldo, Organic Letters, 2001, 3, 2595-2598.) Polymers soluble in polar media and having absorptions from about 450 nm to about 1000 nm can thus be synthesized by incorporation of low bandgap repeat units and pendant polar or charged groups as described herein.

In some embodiments, the polymer is one whose absorbance is not shifted significantly in the presence of target or anionic polynucleotide. Desirably, the polymer exhibits no more than about a 15 nm shift in peak absorbance in the presence of target or anionic polynucleotide; this corresponds to no more than about a 0.08 eV shift for a peak absorption of 480 nm. The polymer may exhibit a peak absorbance shift of about 20, 15, 12, 10, 8 or 5 nm or less. The polymer may exhibit a peak absorbance shift of about 0.10, 0.08, 0.06, 0.04 eV or less. This stability in absorbance can provide desirable properties in bioassays. Polymers whose absorbance shifts excessively depending on assay conditions can lead to undesirable variability.

In some embodiments, a sufficient amount of an appropriate low bandgap repeat unit is incorporated into the CP to render it capable of absorbing energy at a desired wavelength above 450 nm and providing a detectable signal, particularly when localized to a substrate by the sensor. The polymer may include 15 mol %, 20 mol %, 25 mol %, 30 mol %, 35 mol %, 40 mol %, 45 mol %, 50 mol %, 55 mol %, 60 mol %, 65 mol %, 70 mol %, 75 mol %, 80 mol %, 85 mol %, 90 mol %, 95 mol %, or more of the low bandgap repeat unit. In the case of benzothiadiazole-containing polymers, typically greater than about 15 mol % of the repeat units are benzothiadiazole. The exact number of such monomers in the final polymer will depend on its overall length; efficient absorption dictates that the polymer have a plurality of the low bandgap repeat unit.

In some embodiments the polymer can amplify the signal from a fluorophore to which it can transfer energy upon excitation. For example, an alternating copolymer of substituted fluorene monomers and 2,1,3-benzothiadiazole (BT) monomers can provide a five-fold amplification in signal from a Cy-5 labeled sensor when excited at 460 nm as compared to excitation of the fluorophore directly (see examples). As the light gathering abilities of the polymer at this wavelength are directly proportional to the amount of BT monomers, a polymer of this length containing 10 mol % BT monomer would provide the same signal as the fluorophore would in the absence of polymer, and there would be no amplification. Desirably, the polymer is of a length and comprises a sufficient amount of low bandgap repeat units so that upon excitation it transmits sufficient energy to a fluorophore so as to achieve a 50% or greater increase in light emission from the fluorophore than can be achieved by direct excitation of the fluorophore in the absence of polymer.

In the case of copolymers of substituted fluorene and BT monomers, this can be accomplished by incorporating 15 mol % or more of BT monomers in such a polymer. The exact amount of low bandgap repeat unit needed to provide the desired degree of amplification is dependent on a number of factors, and may be determined empirically for a given monomer. Factors to be considered include the length of the polymer, the molar absorptivity of the monomer, and the interaction between the polymer and the biomolecule with which it interacts. The polymer can desirably be of a length and comprise a sufficient amount of an low bandgap repeat unit to provide a two-fold, three-fold, four-fold, five-fold, or greater increase in emission from a fluorophore to which it can transfer energy.

The CP can be a copolymer, and may be a block copolymer, a graft copolymer, or both. A given repeat unit may be incorporated into the polymer randomly, alternately, periodically and/or in blocks.

The particular size of the polymer is not critical, so long as it is able to absorb light in the relevant region. In some embodiments, the polymer (which includes oligomers) also desirably is able to transfer energy to a fluorophore. In some embodiments the polymer has a molecular mass of at least about 1,000 Daltons to allow for efficient interaction with a biomolecule. Typically the polymer will have a molecular mass of about 250,000 Daltons or less. An oligomer has at least two repeats of a chromophoric unit, and may have a plurality of repeats including 3, 4, 5 or more repeats. An oligomer can also comprise a combination of one or more different chromophoric units, each of which independently may or may not be repeated.

In some embodiments the polymer can have a high quantum yield. The polymer may have a quantum yield of greater than about 4% in solution, and may have a quantum yield of up to about 12%. The polymer may exhibit a quantum yield in the solid state of about 4%.

In some embodiments, the polymer may comprise optionally substituted fluorenyl monomers. Polymers comprising fluorenyl monomers exhibiting desirable characteristics and are well studied. However, the absorption profile of fluorene monomers shows absorption at shorter wavelengths than is desired in some embodiments described herein. Thus fluorene copolymers additionally incorporating monomers with lower bandgaps than fluorene may be desirable in some applications described herein.

In some embodiments, the polymer may comprise optionally substituted biphenylene monomers. In some embodiments, the polymer may comprise optionally substituted 2,7-carbazolenevinylene monomers.

The terms "monomer," "monomeric unit" and "repeat unit" are used herein to denote conjugated subunits of a polymer or oligomer. It is to be understood that the repeat units can be incorporated into the polymer at any available position(s) and can be substituted with one or more different groups. Exemplary substituents on the repeat units can be selected from alkyl groups, C1-20 alkyl groups optionally substituted at one or more positions with S, N, O, P or Si atoms, C4-16 alkyl carbonyloxy, C4-16 aryl(trialkylsiloxy), alkoxy, C1-20 alkoxy, cyano, alkylcarbonyloxy, C1-20 alkylcarbonyloxy, and C1-20 thioether.

The CP contains a sufficient density of solubilizing functionalities to render the overall polymer soluble in a polar medium. Exemplary polar media include dimethylsulfoxide (DMSO), dimethylformamide (DMF), ethanol, methanol, isopropanol, dioxane, acetone, acetonitrile, 1-methyl-2-pyrrolidinone, formaldehyde, water, and mixtures comprising these solvents. The CP is desirably soluble in at least one of these polar media, and may be soluble in more than one polar media. The CP preferably contains at least about 0.01 mol % of the solubilizing functionality, and may contain at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or at least about 30 mol %. The CP may contain up to 100 mol % of the solubilizing functionality, and may contain about 99 mol % or less, about 90 mol % or less, about 80 mol % or less, about 70 mol % or less, about 60 mol % or less, about 50 mol % or less, or about 40 mol % or less. Where monomers are polysubstituted, the CP may contain 200 mol %, 300 mol %, 400 mol % or more solubilizing functionalities.

The polymers are desirably polycationic, and any or all of the subunits of the polymer may comprise one or more cationic groups. Any suitable cationic groups may be incorporated. Exemplary cationic groups include ammonium groups, guanidinium groups, histidines, polyamines, pyridinium groups, and sulfonium groups.

Desirably, the CPs described herein are soluble in aqueous solutions and other polar solvents, and preferably are soluble in water. By "water-soluble" is meant that the material exhibits solubility in a predominantly aqueous solution, which, although comprising more than 50% by volume of water, does not exclude other substances from that solution, including without limitation buffers, blocking agents, cosolvents, salts, metal ions and detergents.

One synthetic approach to introducing a charged group into a conjugated polymer is as follows. A neutral polymer can be formed by the Suzuki coupling of one or more bis- (or tris- etc.) boronic acid-substituted monomers with one or more monomers that have at least two bromine substitutions on aromatic ring positions. Bromine groups can also be attached to any or all of the monomers via linkers. Polymer ends can be capped by incorporation of a monobrominated aryl group, for example bromobenzene. Conversion of the polymer to a cationic water-soluble form is accomplished by addition of condensed trimethylamine.

In some embodiments, the CCPs comprise one or more angled linkers with a substitution pattern (or regiochemistry) capable of perturbing the polymers' ability to form rigid-rod structures, allowing the CCPs to have a greater range of three-dimensional structures. The angled linker(s) are optionally substituted aromatic molecules having at least two separate bonds to other polymer components (e.g., monomers, block polymers, end groups) that are capable of forming angles relative to one another which disrupt the overall ability of the polymer to form an extended rigid-rod structure (although significant regions exhibiting such structure may remain). The angled linkers may be bivalent or polyvalent.

The angle which the angled linkers are capable of imparting to the polymeric structure is determined as follows. Where the two bonds to other polymeric components are coplanar, the angle can be determined by extending lines representing those bonds to the point at which they intersect, and then measuring the angle between them. Where the two bonds to other polymeric components are not coplanar, the angle can be determined as follows: a first line is drawn between the two ring atoms to which the bonds attach; two bond lines are drawn, one extending from each ring atom in the direction of its respective bond to the other polymeric component to which it is joined; the angle between each bond line and the first line is fixed; and the two ring atoms are then merged into a single point by shrinking the first line to a zero length; the angle then resulting between the two bond lines is the angle the angled linker imparts to the CCP.

The angle which an angled linker is capable of imparting to the polymer is typically less than about 155°, and may be less than about 1500, less than about 145°, less than about 140°, less than about 135°, less than about 130°, less than about 125°, less than about 120°, less than about 115°, less than about 110°, less than about 105°, less than about 100°, less than about 95°, less than about 90°, less than about 85°, less than about 800, less than about 75°, less than about 70°, less than about 65°, less than about 60°, less than about 55°, or less than about 50°. The angled linker may form an angle to its adjacent polymeric units of about 25°, 30°, 35°, 40°, 45°, 50°, 60° or more. The angled linker may introduce a torsional twist in the conjugated polymer, thereby further disrupting the ability of the polymer to form a rigid-rod structure. For angled linkers having an internally rotatable bond, such as polysubstituted biphenyl, the angled linker must be capable of imparting an angle of less than about 155° in at least one orientation.

For six-membered rings, such angles can be achieved through ortho or meta linkages to the rest of the polymer. For five-membered rings, adjacent linkages fall within this range. For eight-membered rings, linkages extending from adjacent ring atoms, from alternate ring atoms (separated by one ring atom), and from ring atoms separated by two other ring atoms fall within this range. Ring systems with more than eight ring atoms may be used. For polycyclic structures, even more diverse linkage angles can be achieved.

Exemplary linking units which meet these limitations include benzene derivatives incorporated into the polymer in the 1, 2 or 1,3-positions; naphthalene derivatives incorporated into the polymer in the 1,2-, 1,3-, 1,6-, 1,7-, 1,8-positions; anthracene derivatives incorporated into the polymer in the 1,2-, 1,3-, 1,6-, 1,7-, 1,8-, and 1,9-positions; biphenyl derivatives incorporated into the polymer in the 2,3-, 2,4-, 2,6-, 3,3'-, 3,4-, 3,5-, 2,2'-, 2,3'-, 2,4'-, and 3,4'-positions; and corresponding heterocycles. The position numbers are given with reference to unsubstituted carbon-based rings, but the same relative positions of incorporation in the polymer are encompassed in substituted rings and/or heterocycles should their distribution of substituents change the ring numbering.

The CCP may contain at least about 0.01 mol % of the angled linker, at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or at least about 30 mol %. The CCP may contain about 90 mol % or less, about 80 mol % or less, about 70 mol % or less, about 60 mol % or less, about 50 mol % or less, or about 40 mol % or less.

The CCP may be provided in isolated and/or purified form. Any suitable purification or isolation technique may be used, alone or in combination with any other technique. Exemplary techniques include precipitation, crystallization, sublimation, chromatography, dialysis, extraction, etc.

The Sensor Biomolecule

A sensor biomolecule is employed that can bind to a target biomolecule. Exemplary biomolecules include polysaccharides, polynucleotides, peptides, proteins, etc. The sensor biomolecule can be conjugated to a substrate. The sensor may also interact at least in part electrostatically with a polycationic multichromophore, which may be a conjugated polymer. The sensor biomolecule, the target biomolecule, and the multichromophore when bound together form a detection complex. In some embodiments, a sensor polynucleotide is provided that is complementary to a target polynucleotide to be assayed, and which does not interact with the polycationic multichromophore in the absence of target to a degree that precludes the detection of target using the described techniques. Desirably, in some embodiments, the sensor lacks a polyanionic backbone as found in RNA and DNA.

The sensor can be branched, multimeric or circular, but is typically linear, and can contain nonnatural bases. The sensor may be labeled or unlabeled with a detectable moiety.

In some embodiments, the sensor is desirably unlabelled with a moiety that absorbs energy from the multichromophore; particularly, the sensor is unlabelled with a fluorophore or quencher that absorbs energy from an excited state of the multichromophore.

In some embodiments the sensor is labeled with a fluorophore that can absorb energy from the multichromophore and be used in a fluorescence transfer method for detection of polyanionic species.

The sensor may be a PNA, the molecular structures of which are well known. PNAs can be prepared with any desired sequence of bases. Specific sensor PNA structures can be custom-made using commercial sources or chemically synthesized.

Fluorophores

In some embodiments, a fluorophore may be employed, for example to receive energy transferred from an excited state of the polycationic multichromophore or visa versa, or to exchange energy with an polynucleotide-specific dye, or in multiple energy transfer schemes. Fluorophores useful in the inventions described herein include any substance which can absorb energy of an appropriate wavelength and emit light. For multiplexed assays, a plurality of different fluorophores can be used with detectably different emission spectra. Typical fluorophores include fluorescent dyes, semiconductor nanocrystals, lanthanide chelates, and green fluorescent protein.

Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

Exemplary polynucleotide-specific dyes include acridine orange, acridine homodimer, actinomycin D, 7-aminoactinomycin D (7-AAD), 9-amino-6-chloro-2-methoxyacridine (ACMA), BOBO™-1 iodide (462/481), BOBO™-3 iodide (570/602), BO-PRO™-1 iodide (462/481), BO-PRO™-3 iodide (575/599), 4',6-diamidino-2-phenylindole, dihydrochloride (DAPI), 4',6-diamidino-2-phenylindole, dihydrochloride (DAPI), 4',6-diamidino-2-phenylindole, dilactate (DAPI, dilactate), dihydroethidium (hydroethidine), dihydroethidium (hydroethidine), dihydroethidium (hydroethidine), ethidium bromide, ethidium diazide chloride, ethidium homodimer-1 (EthD-1), ethidium homodimer-2 (EthD-2), ethidium monoazide bromide (EMA), hexidium iodide, Hoechst 33258, Hoechst 33342, Hoechst 34580, Hoechst S769121, hydroxystilbamidine, methanesulfonate, JOJO™-1 iodide (529/545), JO-PRO™-1 iodide (530/546), LOLO™-1 iodide (565/579), LO-PRO™-1 iodide (567/580), NeuroTrace™ 435/455, NeuroTrace™ 500/525, NeuroTrace™ 515/535, NeuroTrace™ 530/615, NeuroTrace™ 640/660, OliGreen, PicoGreen® ssDNA, PicoGreen® dsDNA, POPO™-1 iodide (434/456), POPO™-3 iodide (534/570), PO-PRO™-1 iodide (435/455), PO-PRO™-3 iodide (539/567), propidium iodide, RiboGreen®, SlowFade®, SlowFade® Light, SYBR® Green I, SYBR® Green II, SYBR® Gold, SYBR® 101, SYBR® 102, SYBR® 103, SYBR® DX, TO-PRO®-1, TO-PRO®-3, TO-PRO®-5, TOTO®-1, TOTO®-3, YO-PRO®-1 (oxazole yellow), YO-PRO®-3, YOYO®-1, YOYO®-3, TO, SYTOX® Blue, SYTOX® Green, SYTOX® Orange, SYTO® 9, SYTO® BC, SYTO® 40, SYTO® 41, SYTO® 42, SYTO® 43, SYTO® 44, SYTO® 45, SYTO® Blue, SYTO® 11, SYTO® 12, SYTO® 13, SYTO® 14, SYTO® 15, SYTO® 16, SYTO® 20, SYTO® 21, SYTO® 22, SYTO® 23, SYTO® 24, SYTO® 25, SYTO® Green, SYTO® 80, SYTO® 81, SYTO® 82, SYTO® 83, SYTO® 84, SYTO® 85, SYTO® Orange, SYTO® 17, SYTO® 59, SYTO® 60, SYTO® 61, SYTO® 62, SYTO® 63, SYTO® 64, SYTO® Red, netropsin, distamycin, acridine orange, 3,4-benzopyrene, thiazole orange, TOMEHE, daunomycin, acridine, pentyl-TOTAB, and butyl-TOTIN. Asymmetric cyanine dyes may be used as the polynucleotide-specific dye. Other dyes of interest include those described by Geierstanger, B. H. and Wemmer, D. E., Annu. Rev. Vioshys. Biomol. Struct. 1995, 24, 463-493, by Larson, C. J. and Verdine, G. L., Bioorganic Chemistry: Nucleic Acids, Hecht, S. M., Ed., Oxford University Press: New York, 1996; pp 324-346, and by Glumoff, T. and Goldman, A. Nucleic Acids in Chemistry and Biology, $2^{nd}$ ed., Blackburn, G. M. and Gait, M. J., Eds., Oxford University Press: Oxford, 1996, pp 375-441. The polynucleotide-specific dye may be an intercalating dye, and may be specific for double-stranded polynucleotides. Other dyes and fluorophores are described at www.probes.com (Molecular Probes, Inc.).

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R. et al. (1994) Proc. Natl. Acad. Sci. USA 91:12501-12504; Heim, R. et al. (1995) Nature 373: 663-664). Delgrave et al. isolated mutants of cloned *Aequorea victoria* GFP that had red-shifted excitation spectra. Bio/Technology 13:151-154 (1995). Heim, R. et al. reported a mutant (Tyr66 to His) having a blue fluorescence (Proc. Natl. Acad. Sci. (1994) USA 91:12501-12504).

The Substrate

In some embodiments, the sensor is desirably located upon a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly) tetrafluoroethylene, (poly)vinylidenedifluoride, polystyrene, cross-linked polystyrene, polyacrylic, polylactic acid, polyglycolic acid, poly(lactide coglycolide), polyanhydrides, poly (methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of a photodiode, an optoelectronic sensor such as an optoelectronic semiconductor chip or optoelectronic thin-film semiconductor, or a biochip. The location(s) of the individual sensor polynucleotide(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which a sensor polynucleotide or other assay component is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

Sensor polynucleotides can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl. No. PCT/US93/04145 and pin based methods such as those described in U.S. Pat. No. 5,288,514.

Additional flow channel or spotting methods applicable to attachment of sensor polynucleotides to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Excitation and Detection

Any instrument that provides a wavelength that can excite the polycationic multichromophore and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of the signaling chromophore upon excitation of the multichromophore. Incident light wavelengths useful for excitation of conjugated polymers including a plurality of low bandgap repeat units can include 450 nm to 1000 nm wavelength light. Exemplary useful incident light wavelengths include, but are not limited to, wavelengths of at least about 450, 500, 550, 600, 700, 800 or 900 nm, and may be less than about 1000, 900, 800, 700, 600, 550 or 500 nm. Exemplary useful incident light in the region of 450 nm to 500 nm, 500 nm to 550 nm, 550 nm to 600 nm, 600 nm to 700 nm, and 700 nm to 1000 nm. In certain embodiments the polymer forms an excited state upon contact with incident light having a wavelength including a wavelength of about 488 nm, about 532 nm, about 594 nm and/or about 633 nm. Additionally, useful incident light wavelengths can include, but are not limited to, 488 nm, 532 nm, 594 nm and 633 nm wavelength light.

Compositions of Matter

Also provided are compositions of matter of any of the molecules described herein in any of various forms. The polymers described herein may be provided in purified and/or isolated form. The polymers may be provided in crystalline form. The polymers may be provided in solution, which may be a predominantly aqueous solution, which may comprise one or more of the additional solution components described herein, including without limitation additional solvents, buffers, biomolecules, polynucleotides, fluorophores, etc. The polymers may be provided in the form of a film. The compositions of matter may be claimed by any property described herein, including by proposed structure, by method of synthesis, by absorption and/or emission spectrum, by elemental analysis, by NMR spectra, or by any other property or characteristic.

Methods of Use

The polymers provided herein may be employed in a variety of biological assays. They may be used in assays with sensor biomolecules that do not comprise a fluorophore that can exchange energy with the conjugated polymer. The polymer binds at least in part electrostatically to a target biomolecule. The target biomolecule, which may be a polynucleotide, may be labeled or unlabeled. The sensor may be bound to a substrate.

The novel polymers may also be used in biological assays in which energy is transferred between one or more of the polymer, a label on the target biomolecule, a label on the sensor biomolecule, and/or a fluorescent dye specific for a polynucleotide, in all permutations. The polymer may interact at least in part electrostatically with the sensor and/or the target to form additional complexes, and an increase in energy transfer with the polymer may occur upon binding of the sensor and the target. This method may also be performed on a substrate.

Other variations of such methods are described further herein. In one embodiment a single nucleotide polymorphism (SNP) is detected in a target. In another embodiment expression of a gene is detected in a target. In a further embodiment, a measured result of detecting an increase in association of a multichromophore with a substrate can be used to diagnose a disease state of a patient. In yet another embodiment the detection method of the invention can further include a method of diagnosing a disease state. In a related embodiment, the method of diagnosing a disease can include reviewing or analyzing data relating to the level of association of the multichromophore with the substrate and providing a conclusion to a patient, a health care provider or a health care manager, the conclusion being based on the review or analysis of data regarding a disease diagnosis. Reviewing or analyzing such data can be facilitated using a computer or other digital device and a network as described herein. It is envisioned that information relating to such data can be transmitted over the network.

Also provided is a method where a surface, which can be a sensor, changes its net charge from neutral to cationic by virtue of binding a cationic multichromophore to its surface by binding of a compound to a biomolecule on the substrate.

Addition of organic solvents in some cases can result in a decrease in background emission by inhibiting nonionic interactions between assay components, for example between the sensor and the multichromophore. The added solvent may be a polar organic solvent, and may be water miscible, for example an alcohol such as methanol, ethanol, propanol or isopropanol. The added solvent may be one that does not adversely affect the ability of the sensor to hybridize to the target in the solution, for example 1-methyl-2-pyrrolidinone. The organic solvent may be added in an amount of about 1%, about 2%, about 5%, about 10%, or more of the total solution, and typically is used within the range of about 0.5-10%. Other components may be incorporated into the assay solution, for example one or more buffers suitable for maintaining a pH satisfactory for the biological molecules and their desired properties (e.g., ability to hybridize).

In one variation a plurality of fluorophores, which may be directly or indirectly attached or recruited to any other of the assay components and/or to a substrate, can be used to exchange energy in an energy transfer scheme. In particular applications, this can provide for significant additional selectivity. For example, a polynucleotide-specific dye can be used as either an initial or second signaling fluorophore, and may be specific for double-stranded sequences. For example, energy can be transferred from an excited cationic multichromophore to the initial signaling fluorophore, which subsequently transfers energy to the second signaling fluorophore, in an overall format that is selective for the target. This cascade of signaling fluorophores can, in principle, be extended to use any number of signaling fluorophores with compatible absorption and emission profiles. In one embodiment of this variation, an intercalating dye that is specific for double-stranded polynucleotides is used as the second signaling fluorophore, and an initial signaling fluorophore that is capable of transferring energy to the second signaling fluorophore is conjugated to the sensor polynucleotide. The intercalating dye provides the added selective requirement that the sensor and target polynucleotides hybridize before it is recruited to the detection complex. In the presence of target, the duplex is formed, the dye is recruited, and excitation of the multichromophore leads to signaling from the second signaling fluorophore. In certain embodiments the methods of using intercalating dye(s) can include steps wherein the intercalating dye(s) is in a solution.

Any effective detection method can be used in the various methods described herein, including optical, spectroscopic, electrical, electrochemical, piezoelectrical, magnetic, Raman scattering, surface plasmon resonance, radiographic, calorimetric, calorimetric, etc. Preferably the sensor is or can be rendered optically detectable to a human and/or a detection device.

The methods described herein may be used with and incorporated into an apparatus. The methods may be used in conjunction with a commercially available device. Exemplary commercially available systems and instruments that can be used in conjunction with an invention disclosed herein include: array systems such as the Affymetrix Genechip® system, Agilent GenePix® Microarray Scanner, Genomic Solutions GeneMachine®, Asper Biotech Genorama™ Quattroimager, and the Bio-Rad VersArray® ChipReader; and real time PCR systems such as the Applied Biosystems 7900HT Fast Real-Time PCR System, ABI PRISM® 7000 Sequence Detection System, Applied Biosystems 7500 Real-Time PCR System, Applied Biosystems 7300 Real-Time PCR System, Applied Biosystems PRISM® 7700, Bio-Rad MyiQ Single-Color Real-Time PCR Detection System, and the Bio-Rad iCycler iQ Real-Time PCR Detection System.

Articles of Manufacture

The CPs can be incorporated into any of various articles of manufacture including optoelectronic or electronic devices, biosensors, diodes, including photodiodes and light-emitting diodes ("LEDs"), optoelectronic semiconductor chips, semiconductor thin-films, and chips, and can be used in array or microarray form. The polymer can be incorporated into a polymeric photoswitch. The polymer can be incorporated into an optical interconnect or a transducer to convert a light signal to an electrical impulse. The CPs can serve as liquid crystal materials. The CPs may be used as electrodes in electrochemical cells, as conductive layers in electrochromic displays, as field effective transistors, and as Schottky diodes.

The CPs can be used as lasing materials. Optically pumped laser emission has been reported from MEH-PPV in dilute solution in an appropriate solvent, in direct analogy with conventional dye lasers [D. Moses, Appl. Phys. Lett. 60, 3215 (1992); U.S. Pat. No. 5,237,582]. Semiconducting polymers in the form of neat undiluted films have been demonstrated as active luminescent materials in solid state lasers [F. Hide, M. A. Diaz-Garcia, B. J. Schwartz, M. R. Andersson, Q. Pei, and A. J. Heeger, Science 273, 1833 (1996); N. Tessler, G. J. Denton, and R. H. Friend, Nature 382, 695 (1996)]. The use of semiconducting polymers as materials for solid state lasers is disclosed in U.S. Pat. No. 5,881,083 issued Mar. 9, 1999 to Diaz-Garcia et al. and titled "Conjugated Polymers as Materials for Solid State Lasers." In semiconducting polymers, the emission is at longer wavelengths than the onset of significant absorption (the Stokes shift) resulting from inter- and intramolecular energy transfer. Thus there is minimal self-absorption of the emitted radiation [F. Hide et al., Science 273, 1833 (1996)], so self-absorption does not make the materials lossy. Moreover, since the absorption and emission are spectrally separated, pumping the excited state via the π to π* transition does not stimulate emission, and an inverted population can be obtained at relatively low pump power.

Light-emitting diodes can be fabricated incorporating one or more layers of CPs, which may serve as conductive layers. Light can be emitted in various ways, e.g., by using one or more transparent or semitransparent electrodes, thereby allowing generated light to exit from the device.

The mechanism of operation of a polymer LED requires that carrier injection be optimized and balanced by matching the electrodes to the electronic structure of the semiconducting polymer. For optimum injection, the work function of the anode should lie at approximately the top of the valence band, $E_v$, (the π-band or highest occupied molecular orbital, HOMO) and the work function of the cathode should lie at approximately the bottom of the conduction band, $E_c$, (the π*-band or lowest unoccupied molecular orbital, LUMO).

LED embodiments include hole-injecting and electron-injecting electrodes. A conductive layer made of a high work function material (above 4.5 eV) may be used as the hole-injecting electrode. Exemplary high work function materials include electronegative metals such as gold or silver, and metal-metal oxide mixtures such as indium-tin oxide. An electron-injecting electrode can be fabricated from a low work function metal or alloy, typically having a work function below 4.3. Exemplary low work function materials include indium, calcium, barium and magnesium. The electrodes can be applied by any suitable method; a number of methods are known to the art (e.g. evaporated, sputtered, or electron-beam evaporation).

In some embodiments, polymer light-emitting diodes have been fabricated using a semiconducting polymer cast from solution in an organic solvent as an emissive layer and a water-soluble (or methanol-soluble) conjugated copolymer as an electron-transport layer (ETL) in the device configuration: ITO (indium tin oxide)/PEDOT (poly(3,4-ethylene dioxythiophene)/emissive polymer/ETL/Ba/Al. The inventors have successfully fabricated multi-layer PLEDs using a semiconducting polymer (red, green or blue emitting), cast from solution in an organic solvent, as the emissive layer and a water-soluble (or methanol-soluble) cationic conjugated copolymer as electron-transport layer. The results demonstrate that devices with the ETL have significantly lower turn-on voltage, higher brightness and improved luminous efficiency.

Although the examples demonstrate the use of an electron-transport layer formed from the soluble conductive polymer, any form of conducting layer can be used. Thus, judicious choice of monomers as described herein can result in polymers with hole-injecting and/or transporting properties, as well as polymers with electron-injecting and/or transporting properties. The device geometry and deposition order can be selected based on the type of conductive polymer being used. More than one type of conductive polymer can be used in the same multilayer device. A multilayer device may include more than one layer of electron-injecting conjugated polymers, more than one layer of hole-injecting conjugated polymers, or at least one layer of a hole-injecting polymer and at least one layer of an electron-injecting conjugated polymer.

In PLEDs, the device efficiency is reduced by cathode quenching since the recombination zone is typically located near the cathode.[20] The addition of an ETL moves the recombination zone away from the cathode and thereby eliminates cathode quenching. In addition, the ETL can serve to block the diffusion of metal atoms, such as barium and calcium, and thereby prevents the generation of quenching centers[20] during the cathode deposition process.

In some embodiments, the principal criteria when a soluble conjugated polymer is used as an electron transport layer (ETL) in polymer light-emitting diodes (PLEDs) are the following: (1) The lowest unoccupied molecular orbital (LUMO) of the ETL must be at an energy close to, or even within the $\pi^*$-band of the emissive semiconducting polymer (so electrons can be injected); and (2) The solvent used for casting the electron injection material must not dissolve the underlying emissive polymer.

Similarly, the principal criteria for a polymer based hole transport layer (HTL) for use in polymer light-emitting diodes (PLEDs) is that the highest occupied molecular orbital (HOMO) of the HTL must be at an energy close to, or even within the valence band of the emissive semiconducting polymer.

Solubility considerations can dictate the deposition order of the particular CPs ans solvents used to produce a desired device configuration. Any number of layers of CPs with different solubilities may be deposited via solution processing by employing these techniques.

The PLEDs comprising CPs described herein can be incorporated in any available display device, including a full color LED display, a cell phone display, a PDA (personal digital assistant), portable combination devices performing multiple functions (phone/PDA/camera/etc.), a flat panel display including a television or a monitor, a computer monitor, a laptop computer, a computer notepad, and an integrated computer-monitor systems. The PLEDs may be incorporated in active or passive matrices.

Figure 9:
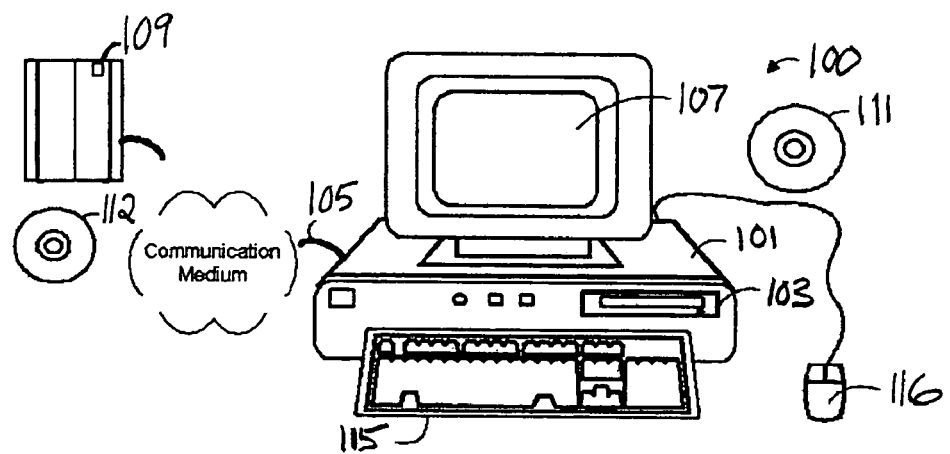
FIG. 9. Block diagram showing a representative example logic device.

FIG. 9 is a block diagram showing a representative example logic device through which reviewing or analyzing data relating to the present invention can be achieved. Such data can be in relation to a disease, disorder or condition in a subject. FIG. 9 shows a computer system (or digital device) 100 that may be understood as a logical apparatus that can read instructions from media 111 and/or network port 105, which can optionally be connected to server 109 having fixed media 112. The system shown in FIG. 9 includes CPU 101, disk drives 103, optional input devices such as keyboard 115 and/or mouse 116 and optional monitor 107. Data communication can be achieved through the indicated communication medium to a server 109 at a local or a remote location. The communication medium can include any means of transmitting and/or receiving data. For example, the communication medium can be a network connection, a wireless connection or an internet connection. It is envisioned that data relating to the present invention can be transmitted over such networks or connections.

In one embodiment, a computer-readable medium includes a medium suitable for transmission of a result of an analysis of a biological sample. The medium can include a result regarding a disease condition or state of a subject, wherein such a result is derived using the methods described herein.

Kits

Kits comprising reagents useful for performing described methods are also provided.

In some embodiments, a kit comprises a polycationic multichromophore as described herein and one or more substrate-bound unlabeled single-stranded sensor polynucleotides that are complementary to corresponding target polynucleotide(s) of interest. In the presence of the target polynucleotide in the sample, the sensor is brought into proximity to the multichromophore upon hybridization to the target, which associates electrostatically with the polycationic multichromophore. Association of the multichromophore with the sensor permits detection and/or quantitation of the target in the sample.

In some embodiments, a kit comprises a polycationic conjugated polymer having an absorption of greater than about 450 nm that can increase signal amplification and one or more sensor biomolecules that can bind to target biomolecule(s) of interest. In these embodiments, association of the multichromophore with the sensor can be directly detected or indirectly detected through energy transfer to or from another species, for example a fluorescent label conjugated to the target and/or a substrate, or to or from an intercalating dye that can intercalate with the sensor-target bound complex.

In some embodiments, a kit comprises an aqueous solution of a polycationic conjugated polymer having an absorption of greater than about 450 nm and one or more sensor biomolecules that can bind to target biomolecule(s) of interest. In these embodiments, association of the multichromophore with the sensor can be directly detected or indirectly detected through energy transfer to another species, for example a fluorescent label conjugated to the target and/or a sensor and/or a substrate to which it may be attached, or to or from an intercalating dye that can intercalate with the sensor-target bound complex.

The kit may optionally contain one or more of the following: one or more labels that can be incorporated into a target; one or more intercalating dyes; one or more sensor biomolecules, one or more substrates which may contain an array, etc.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing which renders the instructions legible. A kit may be in multiplex form for detection of one or more different target polynucleotides or other biomolecules.

Figure 10A:
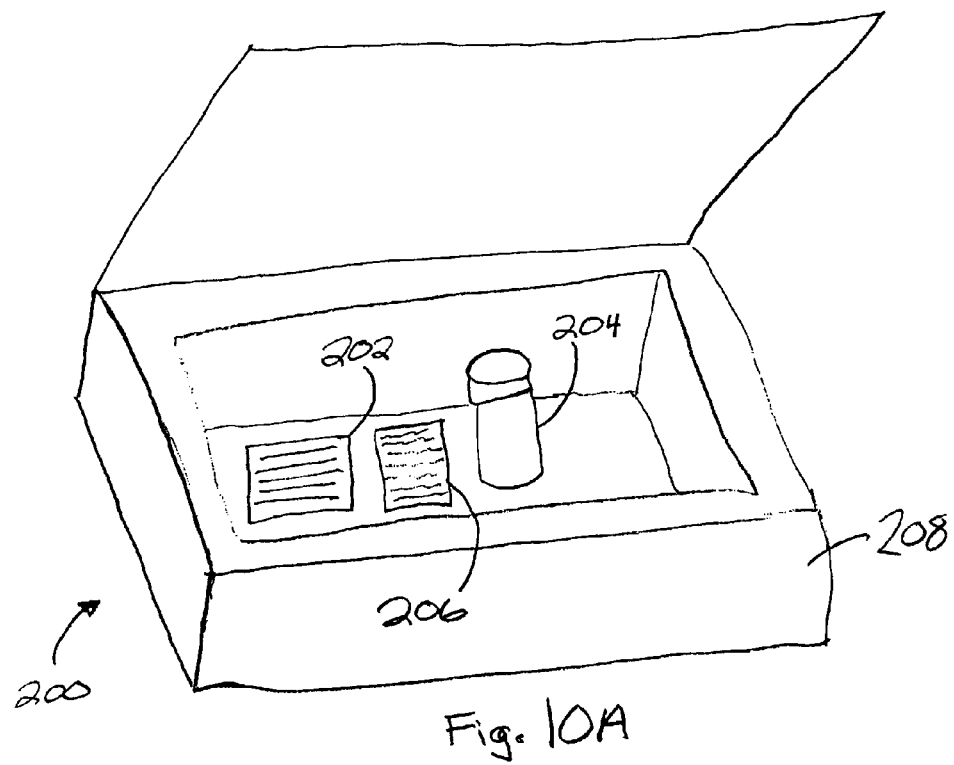
FIGS. 10A and 10B. Block diagrams showing representative examples of a kit.
Figure 10B:
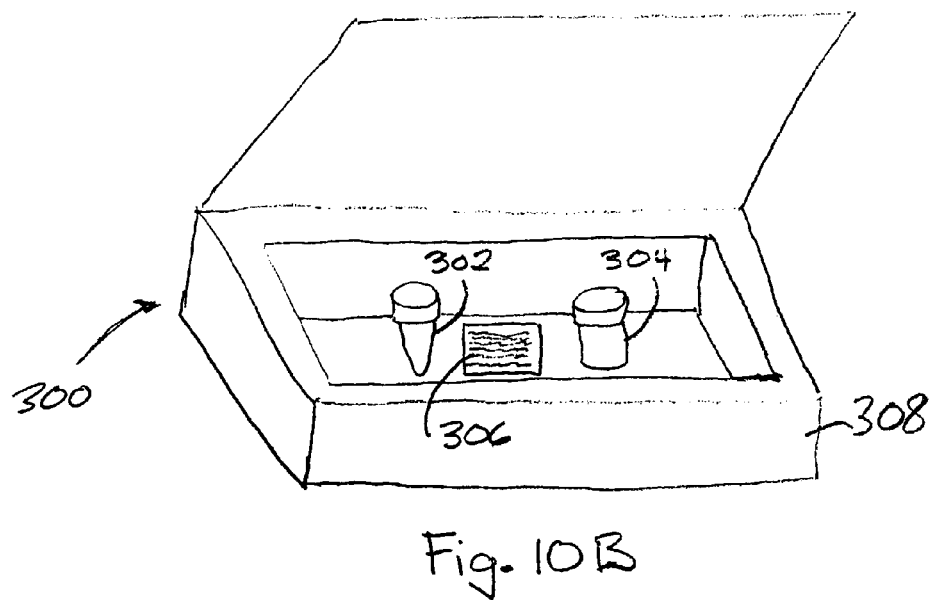
Figure 11:
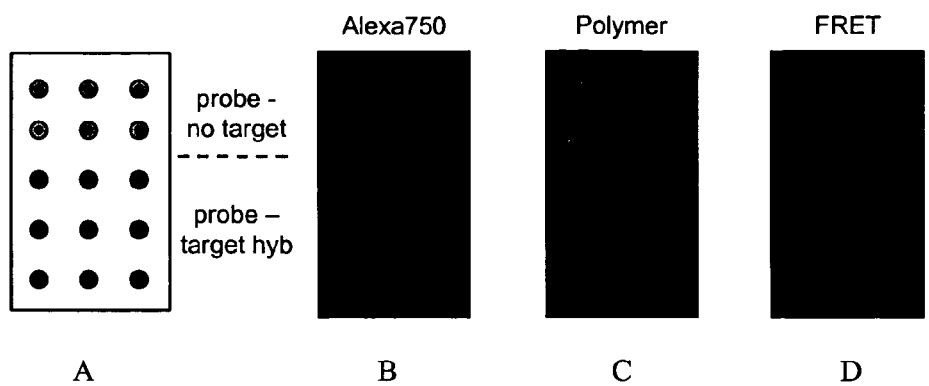
FIG. 11: (A) Emission profile of a DNA probe slide hybridized with Alexa 750 labeled complimentary DNA. Panel A showed the profile of all the spots on the slide. The top two rows had only probe DNA but not the Alexa 750 labeled target and the bottom three rows had both the probe DNA and the hybridized Alexa 750 labeled target. Panel B showed the emission of Alexa 750 at 780 nm when excited at a wavelength of 633 nm. Panel C showed the polymer emission at 578 nm when excited at a wavelength of 488 nm. Panel D showed the fluorescence energy transfer (FRET) of the polymer PFBT to Alexa 750. In Panel D the excitation wavelength used was 488 nm and emission wavelength used was 780 nm. (B) Comparison of Alex 750 and FRET signal intensity. Spots 1 to 6 (upper two rows in FIG. 11A) had no Alexa 750 labeled target. Spots 7 to 15 (lower two rows in FIG. 11A) were hybridized Alexa 750 labeled target. The Alexa 750 signals generated by FRET were over 50% more intense than those generated by direct Alexa 750 excitation.
Figure 11:
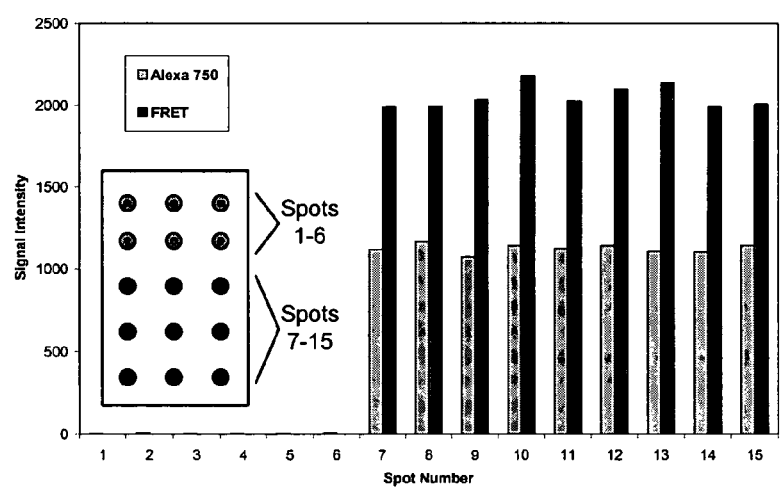
Figure 12:
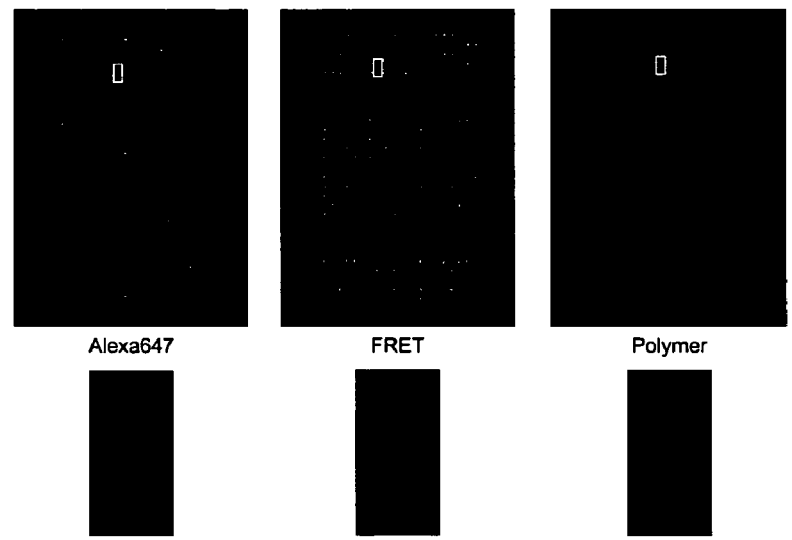
FIG. 12: MWG genome starter arrays tested with PFBT polymer using Alexa647 labeled cDNA. (A) Array image obtained on a Perkin Elmer ProScanArray. Alexa647 signals were obtained with an excitation wavelength of 633 nm and an emission wavelength of 670 nm using a laser setting of 80% and a PMT gain setting of 50%. Polymer signals were obtained with an excitation wavelength of 488 nm and an emission wavelength of 578 nm using a laser setting of 80% and a PMT gain setting of 35%. FRET signals were obtained with an excitation wavelength of 488 nm and an emission wavelength of 670 nm using a laser setting of 80% and a PMT gain setting of 35%. (B) Mean signal intensity of the Alexa647 spots relative to the Alexa647 spots excited using energy transfer from the PFBT polymer (FRET). A crosstalk correction between the PFBT and Alexa647 emission was performed by subtracting $⅕^{th}$ of the Polymer signal from the FRET signal. The FRET response is correlated with the amount of bound target labeled with Alexa647.
Figure 12:
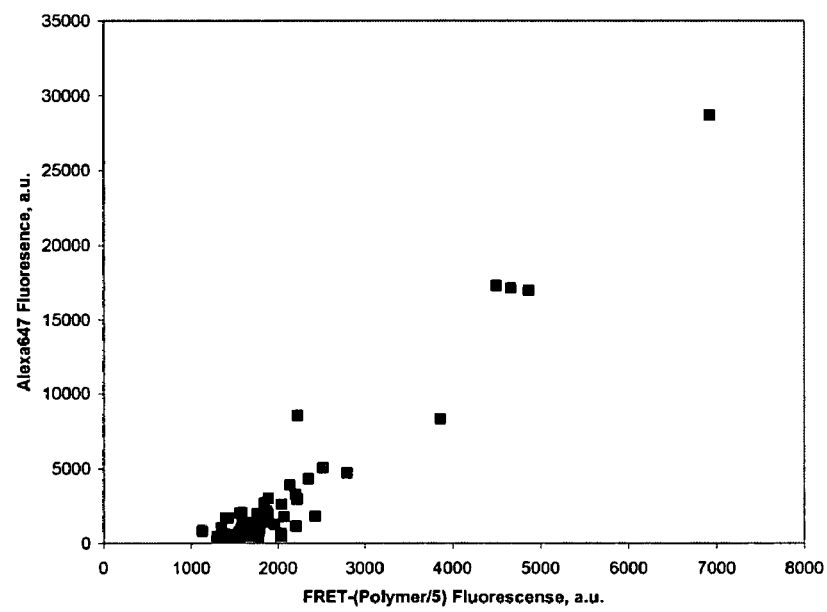

As described herein and shown in FIGS. 10A and 10B, in certain embodiments a kit (200, 300) for assaying a sample is provided. The kit (200, 300) can include a container (208, 308) for containing various components. As shown in FIG. 10B, in one embodiment a kit 300 for assaying a sample for a target includes a container 308, a polymer 304 and a sensor 302. The target can be a biomolecule including but not limited to a polynucleotide. Polymer 304 can include but is not limited to a polycationic conjugated polymer or a dendrimer. In one embodiment polymer 304 is a polycationic multichromophore. Sensor 302 can be a biomolecule including but not limited to a polynucleotide complementary to the target. As shown in FIG. 10A, in one embodiment, kit 200 includes a container 208, a polymer 204 and a sensor 202 conjugated to a substrate. Polymer 204 can include but is not limited to a polycationic conjugated polymer or a dendrimer. In one embodiment, polymer 204 is a polycationic multichromophore. Sensor 202 can be a biomolecule including but not limited to a polynucleotide complementary to the target. As shown in FIGS. 10A and 10B, the kit (200, 300) can optionally include instructions (206, 306) for using the kit (200, 300). Other embodiments of the kit (200, 300) are envisioned wherein the components include various additional features described herein.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Synthesis of 2,7-bis[9,9'-bis(6"-bromohexyl)-fluorenyl]-4,4,5,5-tetramethyl-[1.3.2]dioxaborolane A 50 mL round bottomed flask was charged with 9,9'-bis(bromohexyl)-2,7-dibromofluorene (0.65 g, 1 mmol) in 20 mL of dry THF and cooled to −78° C. with a dry ice/acetone bath. At −78° C., 3 eq. of t-BuLi in pentane (1.8 mL, 1.7 M) was added drop by drop and it was followed immediately by adding 2-isopropoxy-4,4,5,5-tetramethyl-[1.3.2]-dioxabororane (1.3 mL, 6 mol) in one shot. The resulting solution was slowly warmed to room temperature and stirred overnight. It was quenched by water, and the solution was concentrated by rotary evaporation and extracted with chloroform. The organic phase was separated and dried over magnesium sulfate. After evaporation, the reside was purified with silica gel column chromatography (ethyl acetate/hexane 1:20) to yield 0.15 g (20%) of the product as white crystals. $^1$H-NMR (400 MHz, CDCl$_3$): δ 7.83-7.72 (m, 6H), 3.27-3.24 (t, J=6.8 Hz, 4H), 2.03-1.99 (q, J=4.0 Hz, 4H), 1.64-1.57 (q, J=7.2 Hz, 4H), 1.39 (s, 24H), 1.17-1.13 (q, 4H), 1.06-1.02 (q, 4H), 0.55 (m, 4H). This monomer is within the scope of the invention, and may be claimed by its proposed structure described herein, by its method of production,

Example 2

Synthesis of PFBT

The synthesis of poly[9,9'-bis(6"-N,N,N-trimethylammonium)hexyl)fluorene-co-alt-4,7-(2,1,3-benzothiadiazole)dibromide] ("PFBT") is shown in Scheme 1. Suzuki copolymerization of 2,7-bis[9,9'-bis(6"-bromohexyl)-fluorenyl]-4,4,5,5-tetramethyl-[1.3.2]dioxaborolane and 4,7-dibromo-2,1,3-benzothiadiazole gives poly[9,9'-bis(6"-bromohexyl) fluorene-co-alt-4,7-(2,1,3-benzothiadiazole)] in 65% yield.[17] The resulting polymer was purified by three times precipitation from chloroform to methanol. Elemental analysis and $^1$H and $^{13}$C NMR spectroscopies are consistent with the structure in Scheme 1. Gel permeation chromatography shows a number average molecular weight of 12,000 and a PDI of 1.7, relative to polystyrene standards. In a second step, nucleophilic displacement using trimethylamine generates the cationic charges on the polymer pendant groups and produces PFBT, which is soluble in aqueous media.

Scheme 1.

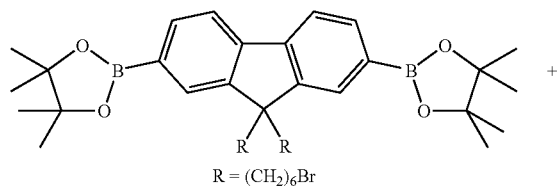

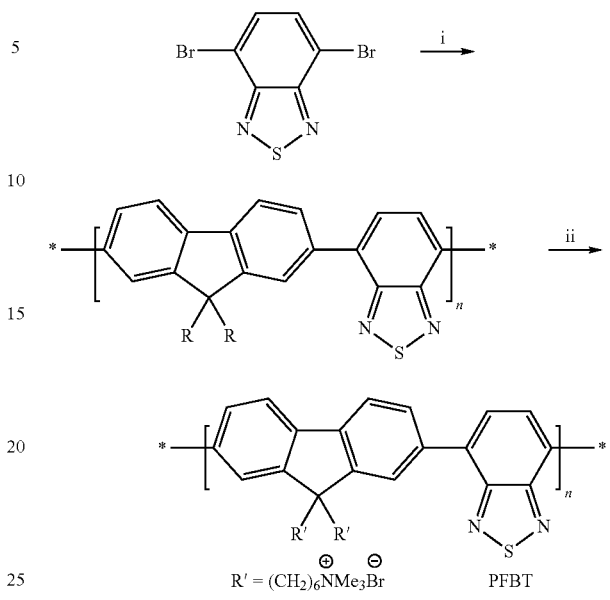

Reaction conditions: i) 2M K$_2$CO$_3$, toluene, Pd(PPh$_3$)$_4$; ii) NMe$_3$, THF/H$_2$O.

Poly[9,9'-bis(6'-bromohexyl)fluorene-co-alt-4,7-(2,1,3-benzothiadiazole)] (PFBT precursor) was synthesized as follows. 2,7-Bis[9,9'-bis(6"-bromohexyl)fluorenyl]-4,4,5,5-tetramethyl-[1.3.2]dioxaborolane (186 mg, 0.25 mmol) and 4,7-dibromo-2,1,3-benzothiadiazole (73.5 mg, 0.25 mmol), Pd(PPh$_3$)$_4$ (5 mg) and potassium carbonate (830 mg, 6 mmol) were placed in a 25 mL round bottom flask. A mixture of water (3 mL) and toluene (6 mL) was added to the flask and the reaction vessel was degassed. The resulting mixture was heated at 85° C. for 20 h, and then added to acetone. The polymer was filtered and washed with methanol and acetone, and then dried under vacuum for 24 h to afford PFBT (105 mg, 65%) as a bright yellow powder. $^1$H NMR (200 MHz, CDCl$_3$): δ 8.07-7.91 (m, 6H), 7.87-7.72 (m, 2H) 3.36-3.29 (t, 6H, J=6.6 Hz), 2.19 (m, 4H), 1.7 (m, 4H), 1.3-1.2 (m, 8H), 0.9 (m, 4H). $^{13}$C NMR (50 MHz, CDCl$_3$): δ 154.5, 151.6, 141.2, 136.8, 133.8, 128.5, 124.3, 120.6, 55.6, 40.4, 34.3, 32.9, 29.3, 27.9, 23.9. GPC (THF, polystyrene standard), M$_w$: 20500 g/mol; M$_n$: 12,000 g/mol; PDI: 1.7. Elemental Analysis Calculated: C, 59.43; H, 5.47; N. 4.47 Found: C, 60.13; H, 5.29; N, 3.35.

Poly[9,9'-bis(6"-N,N,N-trimethylammonium)hexyl)fluorene-co-alt-4,7-(2,1,3-benzothiadiazole)dibromide] (PFBT) was synthesized as follows. Condensed trimethylamine (2 mL) was added dropwise to a solution of the neutral precursor polymer (70 mg) in THF (10 mL) at −78° C. The mixture was then allowed to warm up to room temperature. The precipitate was re-dissolved by addition of water (10 mL). After the mixture was cooled down to −78° C., more trimethylamine (2 mL) was added and the mixture was stirred for 24 h at room temperature. After removing most of the solvent, acetone was added to precipitate PFBT (72 mg, 89%) as a light brown powder. $^1$H NMR (200 MHz, CD$_3$OD): δ 8.30-7.80 (m, 8H), 3.3-3.2 (t, 4H), 3.1 (s, 18H), 2.3 (br, 4H), 1.6 (br, 4H), 1.3 (br, 8H), 0.9 (br, 4H). $^{13}$C NMR (50 MHz, CD$_3$OD): δ 155.7, 152.7, 142.7, 138.2, 134.6, 129.9, 125.3, 121.5, 67.8, 56.9, 52.5, 41.4, 30.5, 27.1, 25.2, 23.9.

Example 3

Absorption and Emission Spectra of PFBT

Figure 2:
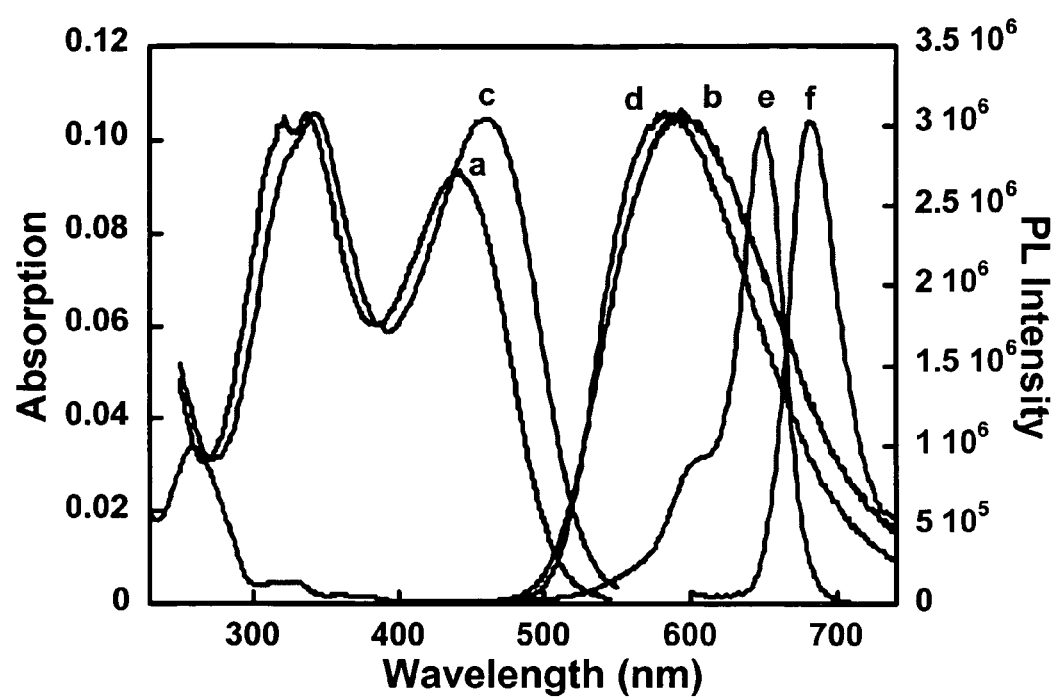
FIG. 2. Normalized absorption (a and c) and photoluminescence (b and d) spectra of PFBT poly[9,9'-bis(6"-N,N,N-trimethylammonium)hexyl)fluorene-co-alt-4,7-(2,1,3-benzothiadiazole)dibromide] in buffer (in black) and in films (in blue). Absorption (e) and emission (f) of $PNA_f$-Cy5 are shown in red. Photoluminescence spectra were obtained by excitation at 460 nm for PFBT and at 645 nm for Cy5. The buffer is 25 mM phosphate buffer, pH=7.4.

FIG. 2 shows the absorption and emission spectra of PFBT in 25 mM phosphate buffer (pH=7.4) and as a film obtained by casting the polymer from a methanol solution (0.005 M). The absorption spectra of PFBT, both in solution and in the solid, display two well-separated bands. The absorption band centered at 330 nm is attributed to the fluorene segments in the polymer, while the absorption at 455 nm corresponds to the contribution from the benzothiadiazole units.[18] The PL spectra for PFBT do not show vibronic structure and display maxima at approximately 590 nm.[19] PFBT has a quantum yield of 10±2% in water (using fluorescein at pH=11 as a standard). The solid-state quantum yield of PFBT was measured to be 4±1% in the solid-state by using an integrating sphere. FIG. 2 also contains the absorption and emission of a Cy-5 labeled PNA (PNA$_f$-Cy5=5'-Cy5-CAGTCCAGT-GATACG-3'; SEQ ID NO: 1). Examination of the 300 to 700 nm range, shows that only PFBT absorbs at 488 and that there is excellent overlap between the emission of PFBT and the absorption of Cy-5, a necessary condition for FRET from PFBT to Cy-5.

Example 4

Use of PFBT for Polynucleotide Detection

Figure 3:
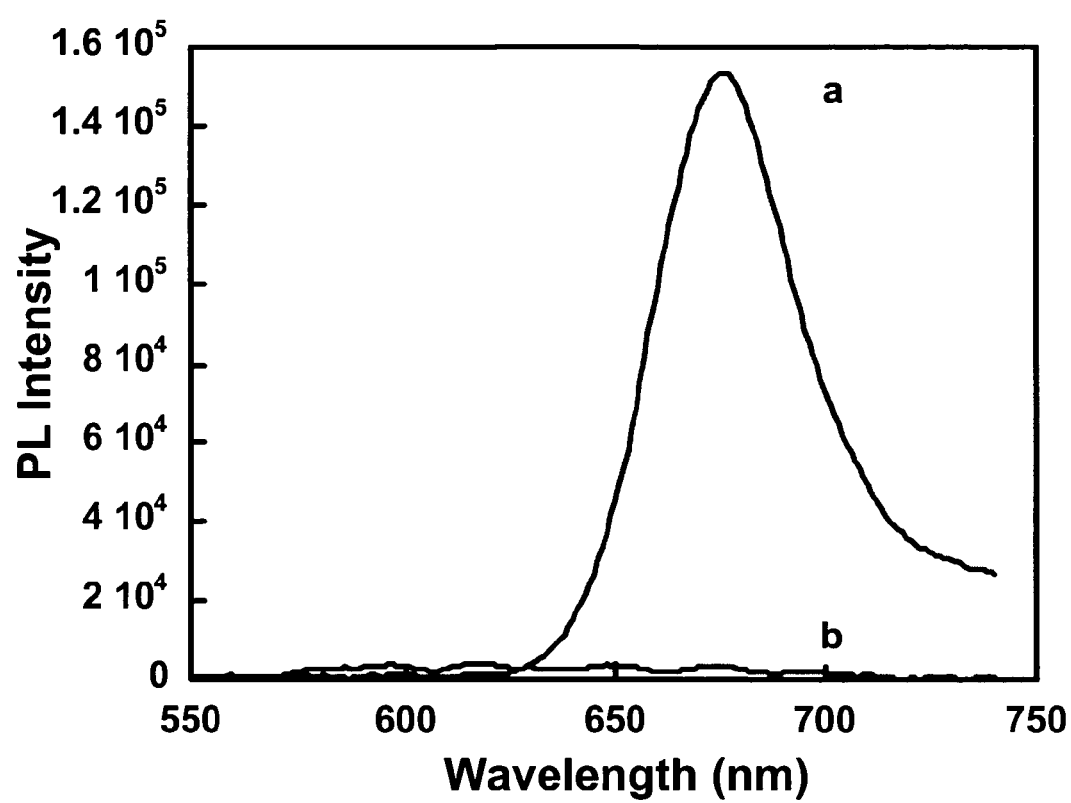
FIG. 3. Photoluminescence spectra of PFBT with (a) hybridized $PNA_f$-Cy5/$ssDNA_f$c and (b) non-hybridized $PNA_f$-Cy5+$ssDNA_f$n in 25 mM phosphate buffer with 5% NMP (excitation wavelength=460 nm, [$PNA_f$-Cy5]=1.0× $10^{-9}$ M). Residual polymer emission was subtracted for clarity.

The use of PFBT ($3.0 \times 10^{-7}$ M in repeat units, RUs) and PNA$_f$-Cy5 ([PNA$_f$-Cy5]=$1 \times 10^{-9}$ M) in the assay shown in FIG. 1 was tested using a complementary ssDNA (ssDNA$_f$c=5'-CGTATCACTGGACTG-3'; SEQ ID NO: 2) and a noncomplementary ssDNA (ssDNA$_f$n=5'-CAGTCTATCGT-CAGT-3'; SEQ ID NO: 3). The experimental conditions chosen include use of a 25 mM phosphate buffer (pH=7.4) with 5% 1-methyl-2-pyrrolidinone (NMP). The small quantity of organic solvent reduces hydrophobic interactions between PNA and PFBT. As shown in FIG. 3, the addition of PFBT to ss-DNA$_f$c/PNA$_f$-Cy5 followed by excitation at 460 nm results in intense red emission from the Cy5. There is no energy transfer for the solution containing ssDNA$_f$n/PNA$_f$-Cy5 under these experimental conditions.

Example 5

Use of PFBT for Detection on a Substrate

Figure 4:
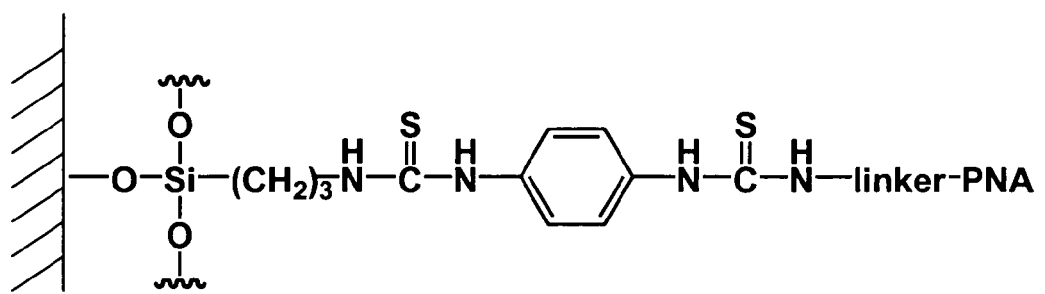
FIG. 4 depicts an embodiment of a surface bound PNA probe structure.

To demonstrate that the signal amplification afforded by the light harvesting properties of PFBT could be incorporated into platforms suitable for microarray technologies, we designed a simplified test structure with PNA probes attached to glass or silica surfaces, as shown in FIG. 4. The test surface was prepared by a sequence of steps that begins with treatment using 2-aminopropyltrimethoxysilane and subsequent activation with 1,4-phenylenediisothiocyanate (PDITC). Amine terminated PNA (PNA$_{II}$=NH$_2$—O—O-TCCACG-GCATCTCA; SEQ ID NO: 4), where O corresponds to a $C_6H_{11}NO_3$ linker fragment, was immobilized on the activated surface by taking advantage of well established isothiocyanate/amine coupling protocols.[20]

To estimate the amount of ssDNA that the PNA-containing surfaces can capture, they were treated with a dye-labeled ssDNA (ssDNA$_{II}$c-Cy5=5'-Cy5-TGAGATGCCGTGGA (SEQ ID NO: 5), [ssDNA$_{II}$c-Cy5]=$3 \times 10^{-7}$ M) solution for 30 minutes at room temperature, followed by washing steps (see Supplementary Information). The resulting quantity of ssDNAc was estimated by measuring the Cy5 fluorescence with a fluoroimager. Comparison of the resulting Cy5 emission intensities against the intensities from a known number of chromophores provided an estimate of $10^{12}$ strands of hybridized ssDNA$_{II}$c-Cy5 per cm$^2$. Cy5 emission was not detected when the surface was treated with the non-complementary ssDNA$_{II}$n-Cy5 (ssDNA$_{II}$n-Cy5=5'-Cy5-ATCTTGACTGT-GTGGGTGCT-3'; SEQ ID NO: 6).

Figure 5:
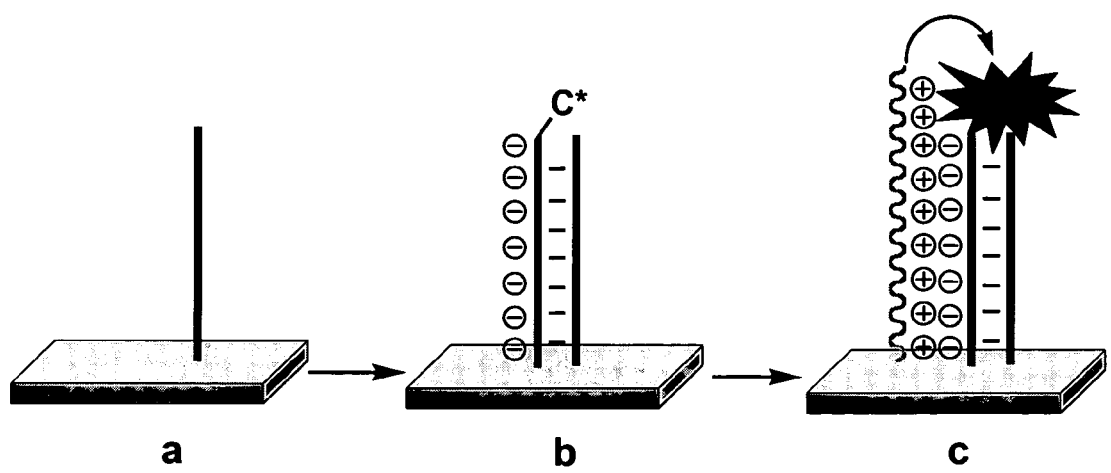
FIG. 5. Amplification of a PNA (black)/ssDNA-C* (red) solid-state sensor by polyelectrolytic deposition of the CCP (orange).

FIG. 5 illustrates the anticipated function of the PNA/CCP assay in the solid-state. Treatment of the PNA (a) containing surface with complementary ssDNA (b, left, shown as polyanionic) increases the negative surface charge. Addition of the CCP results in binding to the surface. Excitation of the polymer results in FRET to the reporter dye. The purpose of the diagram is to show the molecular components in the system and the main recognition/electrostatic events in the sensor operation and not to imply molecular orientations relative to the surface. When non-complementary DNA is used (not shown), the reporter dye is not incorporated onto the surface.

Figure 6:
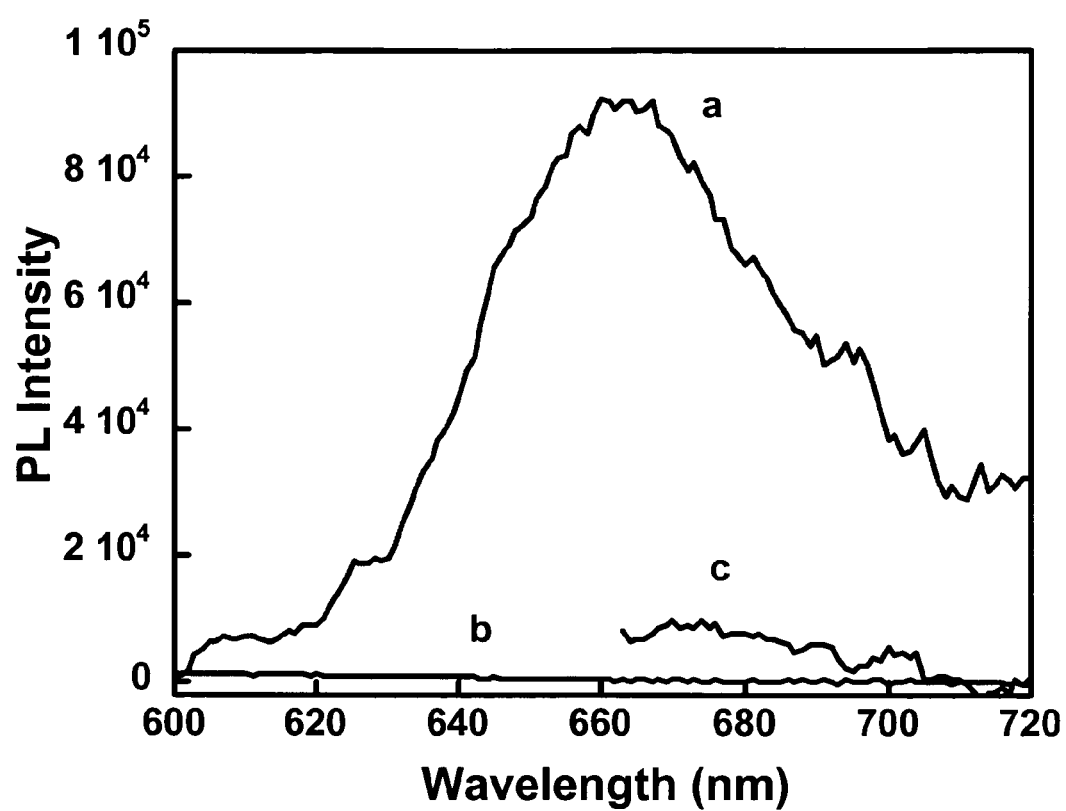
FIG. 6. Fluorescence spectra of (a) $ssDNA_H$c-Cy5/$PNA_H$/PFBT (excitation at 470 nm), (b) $ssDNA_H$n-Cy5/$PNA_H$/PFBT (excitation at 470 nm), (c) $ssDNA_H$c-Cy5/$PNA_H$/PFBT (direct excitation of Cy5 at 645 nm).

FIG. 6 shows the Cy5 emission measured with a standard fluorometer from post-hybridization PNA/DNA substrates after addition of PFBT (1 µL, [PFBT]=$4 \times 10^{-6}$ M). Cy5 emission is clearly detected from the ssDNA$_{II}$c-Cy5/PNA$_{II}$/PFBT surface (a), while none is observed from the ssDNA$_{II}$n-Cy5/PNA$_{II}$/PFBT substrate (b). That Cy5 emission is observed in (a) but not (b) reflects the PNA/DNA selectivity. The additional sensitivity afforded by the addition of PFBT can be established by excitation of the ssDNA$_{II}$c-Cy5/PNA$_{II}$/PFBT surface at 470 nm (PFBT absorption) and at 645 nm (Cy5 absorption maximum). Over an order of magnitude amplification of the dye emission is observed. These results confirm the operation of the sensor as illustrated in FIG. 1.

Example 6

Figure 7:
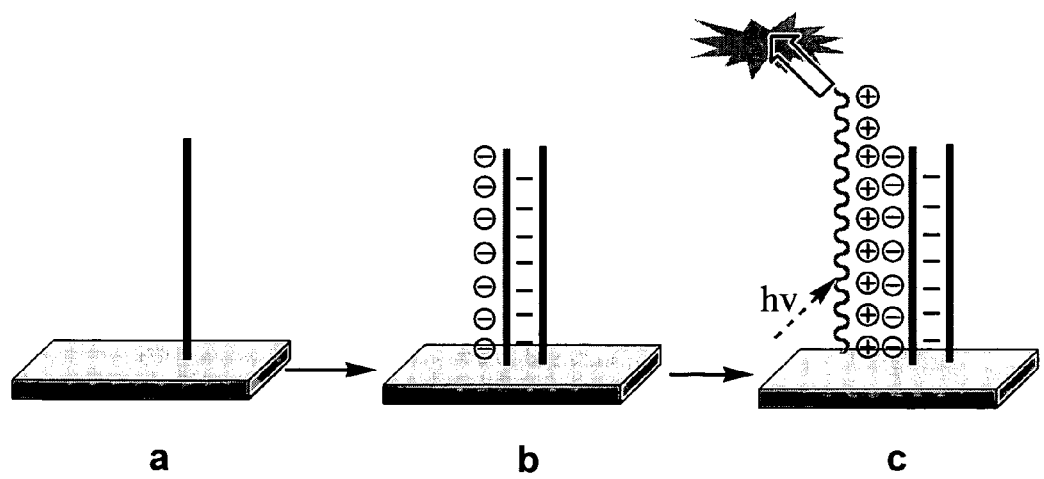
FIG. 7. Hybridization of PNA (a) with ssDNA results in an increase of negative charge at the surface (b). Electrostatic interactions result in adsorption of the CCP (c).

Target Polynucleotide Detection Using a Second Polycationic Multichromophore Because PFBT can be excited at 488 nm and its solid-state emission can be detected with a commercial fluoroimager, it enables a solid-state assay that does not require using labeled sensor polynucleotides for detection of a desired target. The overall process is illustrated in FIG. 7. In one embodiment, hybridization of ssDNA to the PNA surface (FIG. 7a) results in a negatively charged surface (FIG. 7b). Because of electrostatic attraction, the addition of the CCP, followed by washing, should result in preferential adsorption on those sites that contain the complementary ssDNA (FIG. 7c). After workup, polymer emission indicates that the ssDNA is complementary to the PNA sequence. The overall selectivity of FIG. 7 relies on the successful removal of CCP from non-hybridized PNA surfaces.

Figure 8:
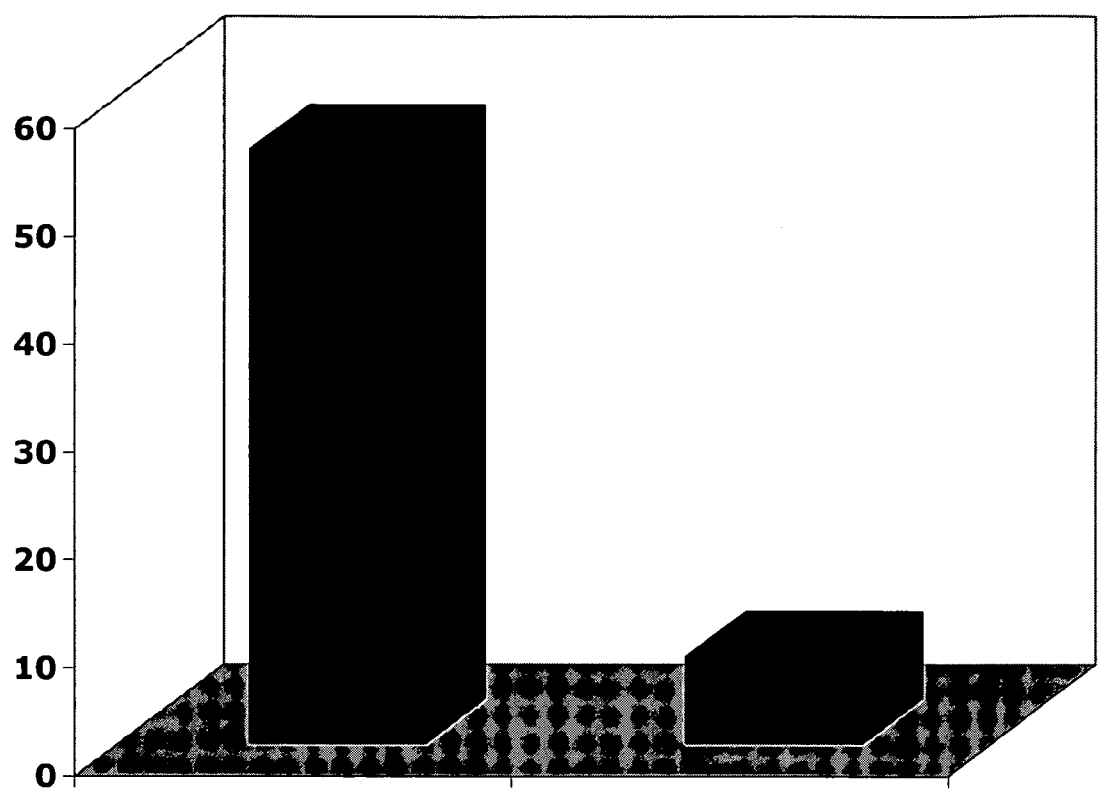
FIG. 8. Comparison of PFBT intensity after 0.5 µL addition to (a) $PNA_H$/$ssDNA_H$c and (b) $PNA_H$/$ssDNA_H$n surfaces, followed by washing. The initial PFBT concentration is $5×10^{-7}$ M.

FIG. 8 shows the integrated PFBT emission from 1 mm$^2$ PNA$_{II}$ surfaces treated according to FIG. 7. The polymer was deposited by addition of 0.5 µL of a $5 \times 10^{-7}$ M solution and was allowed to stand in a hybridization chamber for thirty minutes at room temperature. Washing was accomplished by using SSC (1×)+0.1% SDS solution, followed by SSC (0.1×). When placed inside a fluoroimager one can observe that the PFBT emission from the PNA$_{II}$/ssDNA$_{II}$c surfaces is approximately five times more intense than the emission from the PNA$_{II}$/ssDNA$_{II}$n areas. Exposing the surfaces to more concentrated PFBT solutions results in more intense emission signals, but poorer selectivities. The data in FIG. 8 demonstrate that it is possible to detect the presence of $10^{10}$ ssDNA strands that are complementary to the surface PNA sequence, without the need to label the target species.

Example 7

Use of PFBT for Detection of Polynucleotides on DNA Sensor Arrays

A far-red labeled target polynucleotide was probed using DNA sensors bound to a substrate. When the slide is treated with PFBT polymer those sensor spots which specifically bind a labeled target polynucleotide show increased signal from the target label when the PFBT is excited. Spots without bound target do not show appreciable signal in the wavelength range of the target label allowing one to easily differentiate sensor and target binding events.

Probe Immobilization: Functionalized isothiocyanate slides (SAL-1, Asper Biotech) were used for binding amine terminal sensor molecules. The amino-functionalized DNA (IDT) probe was dissolved in $H_2O$ to a concentration of $1 \times 10^{-4}$ M and then diluted to a final concentration of $5 \times 10^{-5}$ M in 50 mM $Na_2CO_3/NaHCO_3$ buffer (pH 9.0). Spotting was accomplished using 1-μl aliquots with a standard micropipette. Binding of DNA to the surface was performed at 37° C. over a period of 3 hrs inside a humid Corning hybridization chamber containing saturated NaCl solution. After 3 hrs of incubation, the slides were rinsed with DI water followed by rinsing with methanol. The surface was then deactivated in a solution made of dimethylformamide (50 ml) with aminoethanol (0.5 ml) and diisopropylethylamine (1 ml) over a period of 1 hr under shaking. The slides were subsequently washed with dimethylformamide, acetone and water before drying with a flow of nitrogen.

Target hybridization: Target hybridization was performed in the Corning hybridization chamber by using Alexa 750 labeled complimentary DNA at a concentration of $2 \times 10^{-6}$ M in 3×SSC at 42° C. over a period of 16 hrs in darkness. After the 16 hrs incubation, the slide was sequentially washed with 1×SSC/0.1% SDS for 10 min at 42° C., 1×SSC/0.1% SDS for 5 min at 42° C., 0.1×SSC/0.1% SDS for 5 min at room temperature, and 0.1×SSC/0.1% SDS for 5 min at room temperature. The slide was then rinsed with DI water and transferred to a clean tube containing a solution of PFBT polymer.

Polymer Binding: The slide was put into a solution of polymer (about $1 \times 10^{-6}$ M in repeat units) and incubated at room temperature under shaking for 20 min. After incubation in the polymer solution, the slide was washed with 1×SSC for 5 min at room temperature, followed by a water rinse and a methanol wash for 10 min at room temperature. After the methanol wash, the slide was dried under a flow of nitrogen.

Array Scanning: Fluorescence scanning was done on a 4-laser ProScanArray (Perkin Elmer) using a setting of 80% for the laser power and a PMT gain setting of 40%. The excitation wavelength used was 488 nm for the polymer and 633 nm for Alexa 750. Emission of the polymer was measured at 578 nm and the emission of the Alexa 770 was measured at 780 nm. Data analysis was done with the ScanArray Express Microarray Analysis System. Signal obtained was the mean signal intensity of each spot under specific excitation and emission settings. FRET scans were performed using 488 nm excitation and 780 nm emission settings. Sensor spots with bound Alexa 750 labeled target DNA provided a high FRET signal and a lowered polymer signal allowing clear distinction of target bound spots. The FRET signals generated with PFBT polymer excitation provided Alexa 750 signals over 50% greater than the directly excited Alexa 750.

Example 8

Use of PFBT Multichromophore on Substrate Bound Multiplex Detection Probes

To demonstrate the integration of the PFBT multichromophore on a substrate comprised of multiple human genome sensor polynucleotides, a microarray slide was prepared in the following manner and tested on labeled target cDNA:

Target hybridization: Target hybridization was performed on a MWG Human Starter Array slide with a LifterSlip (22× 22 mm) in a Corning hybridization chamber using Alexa 647 labeled human cDNA. The target sample was prepared by diluting 10 ul of the Alexa 647 labeled cDNA with 20 ul of 8×SSPE/1.5% Tween 20 and heated up to 95° C. for 5 min. After a brief spin, the target cDNA was immediately loaded onto the slide using a LifterSlip. The hybridization chamber was quickly assembled and incubated at 42° C. over a period of 16 hrs in darkness. After the 16 hrs incubation, the LifterSlip was first rinsed with 5×SSPE/0.1% Tween 20 at 42° C. and the slide was sequentially washed with 5×SSPE/0.1% Tween 20 for 10 min at 42° C., 5×SSPE/0.1% Tween 20 for 10 min at 42° C., 1×SSPE/0.1% Tween 20 for 10 min at room temperature and three 1 min washes with 0.1×SSPE/0.1% Tween 20 at room temperature. The slide was then rinsed with DI water and incubated in 10% PEG for 2 hrs. After the PEG incubation, the slide was quickly rinsed with water and transferred to a clean tube containing the PFBT polymer solution.

Polymer Binding: The slide was placed into a solution of polymer (about $1 \times 10^{-6}$ M in repeat units) and incubated at room temperature under shaking for 20 min. After incubation in the polymer solution, the slide was washed with 1×SSC for 15 min at 37° C., followed by a 1×SSC rinse, a water rinse and a methanol wash each for 10 min at room temperature. After the methanol wash, the slide was dried under a flow of nitrogen.

Array Scanning: Fluorescence scanning was done on a 4-laser ProScanArray (Perkin Elmer) using a setting of 80% for the laser power. Excitation wavelength used was 488 nm for the polymer and 633 nm for Alexa 647. Emission of the polymer was measured at 578 nm with a PMT gain of 35% and emission of the Alexa 647 was measured at 670 nm with a PMT gain of 50%. Data analysis was done with the ScanArray Express Microarray Analysis System. Signal obtained was the mean signal intensity of each spot under specific excitation and emission settings. FRET scans were performed using 488 nm excitation and 670 nm emission settings with a PMT gain of 35%. Sensor spots binding higher amounts of target cDNA labeled with Alexa647 provided a higher FRET signal and a lower polymer signal allowing clear distinction of target bound spots.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

REFERENCES

[1] Gillespie, D. and Spiegelman, S., J. Mol. Biol. 1965 12, 829.
[2] Lipshutz, R. J.; Fodor, S. P. A.; Gingeras, T. R.; Lockart, D. J., Nature Genet. 1999, 21, 20.
[3] Wolcott, M. J. Clin. Microbiol. Rev. 1992, 5, 370.
[4] (a) Wang, J. Nucleic Acid Res. 2000, 28, 3011. (b) Umek, R. M.; Lin, S. W.; Vielmetter, J.; Terbrueggen, R. H.; Irvine, B.; Yu, C. J.; Kayyem, J. F.; Yowanto, H.; Blackburn, G. F.;

Farkas, D. H.; Chen, Y. P. *J. Mol. Diag.* 2001, 3, 74. (c) Schork N. J.; Fallin D.; Lanchbury J. S. *Clin. Genet.* 2000, 58, 250.

[5] (a) Balakin, K. V.; Korshun, V. A.; Mikhalev, I. I.; Maleev, G. V.; Malakhov A. D.; Prokhorenko, I. A.; Berlin, Yu. A. *Biosensors and Bioelectronics* 1998, 13, 771.

[6] Ranade, K.; Chang, M. S.; Ting, C. T.; Pei, D.; Hsiao, C. F.; Olivier, M.; Pesich, R.; Hebert, J.; Chen, Y. D.; Dzau, V. J.; Curb, D.; Olshen, R.; Risch, N.; Cox, D. R.; Botstein, D., *Genome Res.* 2001, 11, 1262.

[7] Piatek, A. S.; Tyagi, S.; Pol, A. C.; Telenti, A.; Miller, L. P.; Kramer, F. R.; Alland, D., *Nat Biotechnol* 1998, 16, 359.

[8] Service, R. F., *Science* 1988, 282, 396.

[9] Southern, E. M., *Trends Genet.* 1996, 12, 110.

[10] Ramsay, G., *Nature Biotechnol.* 1998, 16, 40.

[11] Epstein, C. B.; Butow, R. A., *Curr. Opin, Biotechnol.*, 2000, 11, 36.

[12] Heeger, P. S.; Heeger, A. J. *Proc. Natl. Acad. Sci. U.S.A.* 1999, 96, 12219. (a) Leclerc, M. *Adv. Mater.* 1999, 11, 1491. (b) McQuade, D. T.; Pullen, A. E.; Swager, T. M. *Chem. Rev.* 2000, 100, 2357. (c) Chen, L.; McBranch, D. W.; Wang, H. L.; Hegelson, R.; Wudl, F.; Whitten, D. C. *Proc. Natl. Acad. Sci. U.S.A.* 1999, 96, 12287.

[13] Lakowicz, J. R.; $2^{nd}$ ed., *Principles of Fluorescence Spectroscopy.* Kluwer Academic/Plenum Publishers. New York, 1999.

[14] (a) Ho, H. A.; Boissinot, M.; Bergeron, M. G.; Corbeil, G.; Doré, K.; Boudreau, D.; Leclerc, M. *Angew. Chem. Int. Ed.* 2002, 41, 1548. (b) Leclerc, M.; Ho, H. A.; Boissinot, M. WO 02/081735 A2, 2002. (c) Peter, K.; Nilsson, R.; Inganäs, O. *Nature Mater.* 2003, 2, 419. (d) Dore K, Dubus S, Ho H A, Levesque I, Brunette M, Corbeil G, Boissinot M, Boivin G, Bergeron M G, Boudreau D, Leclerc M, *J. Am. Chem. Soc.* 2004, 126, 4240.

[15] Kabanov, A. V.; Felgner, P.; Seymour, L. W. Eds. *Self-assembling Complexes for Gene Delivery. From Laboratary to clinical Trial*; John Wiley: Chichester, 1998.

[16] Gaylord, B. S.; Heeger A. J.; Bazan G. C. *Proc. Natl. Acda. Sci, U.S.A.*, 2002, 99, 10954. (b) Gaylord, B. S.; Heeger A. J.; Bazan G. C. *J. Am. Chem. Soc.* 2003, 125, 896. (c) Wang, S.; Bazan, G. C. *Adv. Mater.* 2003, 15, 1425. (d) Liu, B.; Wang, S.; Bazan, G. C.; Mikhailovsky, A. *J. Am. Chem. Soc.* 2003, 125, 13306. (e) Liu, B.; Bazan, G. C. *J. Am. Chem. Soc.* 2004, 126, 1942. (f) Liu, B.; Bazan, G. C. *Chem. Mater.* 2004, 126, 1942.

[17] Liu, B.; Gaylord, B. S.; Wang, S.; Bazan G. C. *J. Am. Chem. Soc.*, 2003, 125, 6705.

[18] Stevens, M. A.; Silva, C.; Russell, D. M.; Friend, R. H. *Phys. Rev.* 2001, 63, 165213

[19] a) Liu, B; Bazan, G. C. *J. Am. Chem. Soc.* 2004, 126, 1942. b) Huang, F.; Hou, L T.; Wu, H. B; Wang X. H.; Shen, H. L.; Cao, W.; Yang, W; Cao, Y. *J. Am. Chem. Soc.* 2004, 126, 9845.

[20] Beier, M.; Hoheisel, J. D. *Nucleic Acids. Res.* 1999, 27, 1970.

---

What is claimed is:

1. An assay method comprising:
providing a sample that is suspected of containing a target polynucleotide;
providing a polycationic multichromophore that comprises a conjugated polymer, wherein said polymer comprises a plurality of low bandgap repeat units sufficient for the polymer to form an excited state when the polymer is contacted with incident light in the region of about 450 nm to about 1000 nm in the absence of the target biomolecule has a detectable excitation emission when excited with light comprising a wavelength in the region of about 450 nm to about 1000 nm;
providing a sensor that is a polynucleotide that is complementary to the target polynucleotide, wherein said sensor is conjugated to a substrate and is not chemically conjugated to a fluorescently detectable label that can receive energy from an excited state of the multichromophore, wherein the target is chemically attached to a fluorescently detectable label that can receive energy from an excited state of the multichromophore;
contacting the substrate with the sample;
contacting the substrate with the multichromophore under conditions wherein the multichromophore can bind to the sensor and/or target polynucleotide, if present; and
detecting whether target has bound to the sensor by detecting whether energy has been transferred from the multichromophore.

2. The method of claim 1, wherein the sensor polynucleotide is DNA.

3. The method of claim 1, wherein the sensor polynucleotide is PNA.

4. The method of claim 1, wherein the multichromophore comprises a conjugated polymer.

5. The method of claim 4, wherein the multichromophore comprises the structure

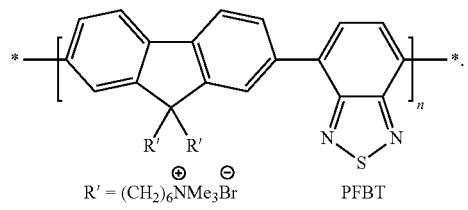

6. The method of claim 1, wherein the sensor is contacted with the multichromophore in the presence of a sufficient amount of an organic solvent to decrease nonionic interactions with the multichromophore.

7. The method of claim 6, wherein the organic solvent is a polar organic solvent.

8. The method of claim 7, wherein the polar organic solvent is miscible with water.

9. The method of claim 1, wherein the target polynucleotide is DNA.

10. The method of claim 1, wherein the target polynucleotide is RNA.

11. The method of claim 1, wherein the target comprises single-stranded polynucleotide.

12. The method of claim 1, wherein the target comprises double-stranded polynucleotide.

13. The method of claim 1, wherein the target polynucleotide is produced via an amplification reaction.

14. The method of claim 1, wherein light emitted above a threshold level indicates that the target polynucleotide is present in the sample.

15. The method of claim 1, wherein the amount of light emitted is quantitated and used to determine the amount of the target polynucleotide in the sample.

16. The method of claim 1, wherein the target polynucleotide is not amplified.

17. A detection method comprising:
providing a sample that is suspected of containing a target biomolecule;
providing a chromophore that comprises a polymer, wherein said polymer comprises a plurality of low bandgap repeat units sufficient for the polymer to form an excited state when the polymer is contacted with incident light in the region of about 450 nm to about 1000 nm in the absence of the target biomolecule, wherein said chromophore has a detectable excitation emission when excited with light having a wavelength in the region of about 450 nm to about 1000 nm, wherein the target is chemically attached to a fluorescently detectable label that can receive energy from an excited state of the chromophore;
providing a sensor biomolecule capable of recognition pairing with the target biomolecule, wherein the sensor is conjugated to a substrate and is not chemically conjugated to a fluorescently detectable label that can receive energy from an excited state of the chromophore;
contacting the substrate with the sample under conditions in which the sensor can pair with the target, if present;
contacting the substrate with the chromophore under conditions wherein the chromophore can bind to the sensor and/or target polynucleotide, if present;
detecting whether target has bound to the sensor by detecting whether energy has been transferred from the chromophore.

18. The method of claim 17, wherein the chromophore is a polycationic multichromophore.

19. The method of claim 17, wherein the substrate is further contacted with an intercalating dye in a solution under conditions in which the dye can intercalate with the sensor and the target when paired.

20. The method of claim 17, wherein the sensor is selected from the group consisting of a peptide and a polynucleotide.

21. The method of claim 20, wherein the sensor is PNA.

22. The method of claim 20, wherein the target is a polynucleotide produced via an amplification reaction.

23. The method of claim 22, wherein the amplification reaction is performed under real-time detection conditions such that detection of pairing between the sensor and the target occurs in real-time.

24. The method of claim 17, wherein the chromophore has a detectable excitation emission when excited with light having a wavelength selected from the group consisting of 450 nm to 500 nm, 500 nm to 550 nm, 550 nm to 600 nm, 600 nm to 700 nm, and 700 nm to 1000 nm.

25. The method of claim 17, wherein the wavelength is selected from the group consisting of about 488 nm, about 532 nm, about 594 nm and about 633 nm.

26. The method of claim 17, wherein the wavelength is about 488 nm.

27. The method of claim 17, wherein a SNP is detected in a target.

28. The method of claim 17, wherein expression of a gene is detected upon detection of the target.

29. The method of claim 17, wherein detecting whether target has bound to the sensor comprises obtaining a result regarding expression of a target biomolecule, wherein said result is used to diagnose a disease state of the source of the sample.

30. The method of claim 29, wherein diagnosing a disease state comprises reviewing or analyzing data relating to the level of association of the chromophore with the substrate; and further comprising
providing a conclusion to a patient, a health care provider or a health care manager, the conclusion being based on the review or analysis of data regarding the disease state.

31. The method of claim 30, wherein providing a conclusion comprises transmission of the data over a network.

32. The method of claim 17, wherein the sensor comprises DNA.

33. The method of claim 17, wherein the target is selected from the group consisting of a peptide and a polynucleotide.

34. The method of claim 17, wherein the target comprises a polynucleotide.

35. The method of claim 17, wherein the target comprises DNA.

36. The method of claim 17, wherein the target comprises RNA.

37. A detection method comprising:
providing a sample that is suspected of containing a polyanionic target comprising single-stranded DNA;
providing a polycationic multichromophore that comprises a conjugated polymer and that electrostatically interacts with the target and has a detectable excitation emission when excited with light comprising a wavelength of about 488 nm, and wherein said polymer comprises a plurality of low bandgap repeat units sufficient for the polymer to form an excited state when the polymer is contacted with incident light in the region of about 450 nm to about 1000 nm in the absence of the target biomolecule;
providing a sensor comprising PNA capable of recognition pairing with the target and not stably associating with the multichromophore in the absence of the target, wherein the sensor is conjugated to a substrate and is not chemically conjugated to a fluorescently detectable label that can receive energy from an excited state of the multichromophore;
contacting the substrate with the sample under conditions in which the sensor can pair with the target, if present;
contacting the substrate with the multichromophore under conditions wherein the multichromophore can bind to the sensor and/or target, if present;
detecting whether target has bound to the sensor.

* * * * *

SEQUENCE LISTING

```
<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cagtccagtg atacg                                                           15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtatcactg gactg                                                           15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtctatcg tcagt                                                           15
```

-continued

```
<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccacggcat ctca                                                         14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgagatgccg tgga                                                         14

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atcttgactg tgtgggtgct                                                   20
```